(12) United States Patent
Xie et al.

(10) Patent No.: US 10,987,669 B2
(45) Date of Patent: Apr. 27, 2021

(54) APPARATUS AND METHOD FOR DETECTION OF TUMOUR CELLS AND CIRCULATING TUMOUR CELLS

(71) Applicants: MEDCOM ADVANCE, S.A., Barcelona (ES); MEDCOM TECH, S.A., Madrid (ES); FUNDACION DE INVESTIGACION HM HOSPITALES, Madrid (ES)

(72) Inventors: Hainan Xie, Tarragona (ES); Manuel Garcia Algar, Tarragona (ES); Moritz Nazarenus, Tarragona (ES); Juan Sagales, Barcelona (ES); Carlos Villanueva Leal, Barcelona (ES); Sara Gomez de Pedro, Tarragona (ES); Eduardo Manuel Garcia Rico, Madrid (ES)

(73) Assignees: MEDCOM TECH, S.A., Madrid (ES); FUNDACION DE INVESTIGACION HM HOSPITALES, Madrid (ES); MEDCOM ADVANCE, S.A., Barcelona (ES)

( * ) Notice: Subject to any disclaimer, the term of this patent is extended or adjusted under 35 U.S.C. 154(b) by 66 days.

(21) Appl. No.: 16/081,720

(22) PCT Filed: Mar. 3, 2017

(86) PCT No.: PCT/EP2017/055023
§ 371 (c)(1),
(2) Date: Aug. 31, 2018

(87) PCT Pub. No.: WO2017/149127
PCT Pub. Date: Sep. 8, 2017

(65) Prior Publication Data
US 2019/0022652 A1    Jan. 24, 2019

(30) Foreign Application Priority Data
Mar. 3, 2016 (EP) .................................. 16382093

(51) Int. Cl.
*G01N 33/52* (2006.01)
*G01N 33/574* (2006.01)
*B01L 3/00* (2006.01)

(52) U.S. Cl.
CPC ........ *B01L 3/502753* (2013.01); *G01N 33/52* (2013.01); *G01N 33/57496* (2013.01); *B01L 2300/0867* (2013.01); *G01N 2800/50* (2013.01); *G01N 2800/52* (2013.01); *G01N 2800/56* (2013.01); *G01N 2800/7028* (2013.01)

(58) Field of Classification Search
CPC .............. G01N 33/52; G01N 2800/50; G01N 2800/52; G01N 2800/56; G01N 2800/7028
See application file for complete search history.

(56) References Cited

FOREIGN PATENT DOCUMENTS

| CN | 107699478 A | 2/2018 |
|---|---|---|
| CN | 107974392 A | 5/2018 |
| WO | WO03066191 A1 | 8/2003 |
| WO | WO2015092726 A1 | 6/2015 |

OTHER PUBLICATIONS

Alix-Panabieres, "Circulating Tumor Cells and Circulating Tumor DNA", "Annual Rev. Med.", 2012, pp. 199-215, vol. 63.
Alix-Panabieres, C., et al., "Technologies for Detection of Circulating Tumor Cells: Facts and Vision", "The Royal Society of Chemistry: Lab on a Chip", 2013, p. 1-6.
Allan, A.L., et al., "Circulating Tumor Cell Analysis: Technical and Statistical Considerations for Application to the Clinic", "Journal of Oncology", 2009, p. 2-10, vol. 2010.
Annibaldi, A., et al., "Glucose Metabolism in Cancer Cells", "Current Opinion in Clinical Nutrition and Metabolic Care", 2010, pp. 466-470, vol. 13.
Cai, H., et al., "2-NBDG Fluorescence Imaging of Hypermetabolic Circulating Tumor Cells in Mouse Xenograft Model of Breast Cancer", "J. Fluoresc", 2013, pp. 213-220, vol. 23.
Chaffer, C.L., et al., "A Perspective on Cancer Cell Metastasis", "Science", Mar. 25, 2011, pp. 1559-1565, vol. 331.
Cox, B.L., et al., "The Sweet Spot: FDG and Other 2-Carbon Glucose Analogs for Multi-Modal Metabolic Imaging of Tumor Metabolism", "Am. J. Nucl. Med.", 2015, pp. 1-13, vol. 5, No. 1.
Crowley, E., et al., "Liquid Biopsy: Monitoring Cancer-Genetics in the Blood", "Nature Reviews: Clinical Oncology", 2013, pp. 1-13.
Ferlay, J., et al., "Cancer Incidence and Mortality Worldwide: Sources, Methods and Major Patterns in GLOBOCAN 2012", "Int. J. Cancer", 2015, pp. E359-E386, vol. 136.
Fidler, I.J., "The Pathogenesis of Cancer Metastasis: The 'Seed and Soil' Hypothesis Revisited", "Nature Revies: Cancer", Jun. 2003, pp. 2-6, vol. 3.
Gu, Y., et al., "Detection of Circulating Tumor Cells in Prostate Cancer Based on Carboxylated Graphene Oxide Modified Light Addressable Potentiometric Sensor", "Biosensors and Bioelectronics", 2015, pp. 24-31, vol. 66.
Heitzer, E., et al., "Circulating Tumor DNA as a Liquid Biopsy for Cancer", "Clinical Chemistry", Nov. 11, 2014, pp. 1-12, vol. 61, No. 1.
Hillig, T., et al., "In Vitro Validation of an Ultra-Sensitive Scanning Fluorescence Microscope for Analysis of Circulating Tumor Cells", "Acta Pathologica Microbiologica Et Immunologica Scandinavica", 2014, pp. 545-551, vol. 122.
Hillig, T., et al., "In Vitro Detection of Circulating Tumor Cells Compared by the CytoTrack and CellSearch Methods", "Tumor Biol.", 2015, pp. 4597-4601, vol. 36.

(Continued)

*Primary Examiner* — Taeyoon Kim
(74) *Attorney, Agent, or Firm* — Hultquist, PLLC; Steven J. Hultquist

(57) ABSTRACT

The invention relates to an apparatus and method of detecting and quantifying the number of circulating tumour cells (CTCs) and/or tumour cells (TCs) from a liquid biopsy by using a hyperoxic environment and incubation with a fluorophore-labelled metabolic indicator (fluorophore-labelled 2-D-glucose derivative) and microfluidic chips.

4 Claims, 8 Drawing Sheets

(56) References Cited

OTHER PUBLICATIONS

Icard, P., et al., "A Global View of the Biochemical Pathways Involved in the Regulation of the Metabolism of Cancer Cells", "Biochimica et Biophysica Acta", 2012, pp. 423-433, vol. 1826.
Joosse, S.A., et al., "Biology, Detection, and Clinical Implications of Circulating Tumor Cells", "EMBO Molecular Medicine", Nov. 14, 2014, pp. 1-11, vol. 7, No. 1.
Li, P., et al., "Acoustic Separation of Circulating Tumor Cells", "PNAS Early Edition", 2015, pp. 1-6.
Liu, M.C., et al., "Circulating Tumor Cells: A Useful Predictor of Treatment Efficacy in Metastatic Breast Cancer", "Journal of Clinical Oncology", Nov. 1, 2009, pp. 5153-5159, vol. 27, No. 31.
Mehendale, N.D., et al., "Proceedings of the 2014 COMSOL Conference", 2014, pp. 1-7.
Millon, S.R., et al., "Uptake of 2-NBDG as a Method to Monitor Therapy Response in Breast Cancer Cell Lines", "Breast Cancer Res Treat", 2011, pp. 55-62, vol. 126.
O'Neil, R.G., et al., "Uptake of a Fluorescent Deoxyglucose Analog (2-NBDG) in Tumor Cells", "Mol. Imaging Biol", 2005, pp. 388-392, vol. 7.
Pallaoro, A., et al., "Rapid Identification by Surface Enhanced Raman Spectroscopy of Cancer Cells at Low Concentrate Flowing in a Microfluidic Channel", "ACS Nano", 2015, pp. 1-29.
Rolfo, C., et al., "Liquid Biopsies in Lung Cancer: The New Ambrosia of Researchers", "Biochimica et Biophysica Acta", 2014, pp. 539-546, vol. 1846.
Schwarzenbach, H., et al., "Cell-Free Nucleic Acids as Biomarkers in Cancer Patients", "Nature Reviews: Cancer", Jun. 2011, pp. 426-437, vol. 11.
Takahashi, S., et al., "Role of Sodium and Potassium Ions in Regulation of Glucose Metabolism in Cultured Astroglia", "Proc. Natl. Acad. Sci.", May 1995, pp. 4616-4620, vol. 92.
Tewes, M., et al., "Detection of Disseminated Tumor Cells in Bone Marrow and Circulating Tumor Cells in Blood of Patients with Early-Stage Male Breast Cancer", "J. Cancer Research Clin Oncol", 2015, pp. 87-92, vol. 141.
Van Dalum, G., et al., "Importance of Circulating Tumor Cells in Newly Diagnosed Colorectal Cancer", "International Journal of Oncology", 2015, pp. 1361-1368, vol. 46.
Van Dalum, G., et al., "Circulating Tumor Cells Before and During Follow-Up After Breast Cancer Surgery", "International Journal of Oncology", 2015, pp. 407-413, vol. 46.
Xiong, B., et al., "Recent Developments in Microfluidics for Cell Studies", "Adv. Mater.", 2014, pp. 1-8.
Yamada, K., et al., "A Real-Time Method of Imaging Glucose Uptake in Single, Living Mammalian Cells", "Nature Protocols", 2007, pp. 753-762, vol. 2, No. 3.
Yu, M., et al., "Circulating Tumor Cells: Approaches to Isolation and Characterization", "J. Cell Biol.", 2011, pp. 373-382, vol. 192, No. 3.
Zheng, D., et al., "2-Deoxy-D-Glucose Targeting of Glucose Metabolism in Cancer Cells as a Potential Therapy", "Cancer Letters", 2014, pp. 176-183, vol. 355.
Zou, C. et al., "2-NBDG as a Fluorescent Indicator for Direct Glucose Uptake Measurement", "J. Biochem. Biophys. Methods", 2005, pp. 207-215, vol. 64.
Fernandez-Carrascal, A., et al., "Metabolic Pathway for the Universal Fluorescent Recognition of Tumor Cells", "Oncotarget", 2017, pp. 76108-76115, vol. 8, No. 44.

APPARATUS AND METHOD FOR DETECTION OF TUMOUR CELLS AND CIRCULATING TUMOUR CELLS

CROSS-REFERENCE TO RELATED APPLICATIONS

This is a U.S. national phase under the provisions of 35 U.S.C. §371 of International Patent Application No. PCT/EP17/55023 filed Mar. 3, 2017, which in turn claims priority under 35 U.S.C. §119 of European Patent Application No. 16382093.9 filed Mar. 3, 2016. The disclosures of such international patent application and European priority patent application are hereby incorporated herein by reference in their respective entireties, for all purposes.

TECHNICAL FIELD OF THE INVENTION

This invention relates to the field of cancer, specifically to an apparatus and method of detecting and quantifying the number of tumour cells (TCs) and/or circulating tumour cells (CTCs) from a liquid biopsy by using a hyperoxic environment, a fluorophore-labelled metabolic indicator (fluorophore-labelled 2-D-glucose derivative) and microfluidic chips.

BACKGROUND OF THE INVENTION

Cancer generally associates with the deterioration of patient's life quality and expectancy. Unfortunately, in the year 2012, approximately 14.1 million people across the world were diagnosed with various types of cancers and 8 million people died from cancer. Metastasis is responsible for most (greater than 90%) cancer-associated mortality. During metastatic dissemination, a tumour cell detaches from a primary tumour and locally invades the surrounding tissue, enters the microvasculature of the lymph and blood systems (intravasation), survives and translocates largely through the bloodstream to microvessels of distant tissues, exits from the bloodstream (extravasation), survives in the microenvironment of distant tissues, and finally adapts to the foreign microenvironment of these tissues in ways that facilitate cell proliferation and the formation of a macroscopic secondary tumour (colonization) (Fidler, I. J. *Nature Reviews Cancer,* 2003, 3,453). Tumour cells that are identified in transit within the bloodstream are referred to as circulating tumour cells (CTCs) and they are found in the blood of majority of patients with advanced primary carcinomas. The enumeration of CTCs has been demonstrated as an effective prognostic marker and predictor of therapy efficiency in various types of advanced cancers (Allan, A. L.; Keeney, M. *Journal of Oncology,* 2010, 2010, 426218). For example, five or more CTCs per 7.5 mL of blood indicates poorer progression-free survival (PFS) in patients with metastatic breast cancer (MBC) (Liu, M. C. et al. *Journal of Clinical Oncology,* 2009, 27, 5153). However, CTCs are extraordinarily rare estimated at one tumour cell in the background of $10^8$–$10^9$ of white blood cells. Therefore, their identification and characterization require extremely sensitive and specific analytical methods. Since the detection of rare events is always hampered by the problems of the Poisson statistics, the analysis of a larger blood volume (at least 7.5 mL or more) is preferable, in particular, in early-stage cancer patients with a small burden of CTCs.

Liquid biopsy focuses on the detection and characterization of CTCs offering the opportunity to investigate primary tumour as well as metastasis. Unlike traditional biopsies taken from the tumour site directly by surgery which may occur myriad practical issues, liquid biopsy is a non-invasive blood test and allows diagnosing the type of cancer when primary tumour is not accessible or does not appear. More importantly, liquid biopsy enables the prediction of disease progression and provides an overall vision of the tumour, while in the case of traditional biopsies only a snap-shot of the ensemble situation can be obtained (Crowley E. et al. *Nature Reviews Clinical Oncology* 2013, 10, 472).

Currently, the most prevalent CTC detection strategy is based on targeting the tumour associated antigens such as the use of antibodies against the epithelial cell adhesion molecule (EpCAM) for capturing CTCs (Alix-Panabières, C. et al. *Annual Review of Medicine,* 2012, 63, 199). Consequently, CTCs with low or absent expression of EpCAM are easily missed. However, the progression of a malignant tumour is really complicated. Through a proposed process known as the epithelial-mesenchymal transition (EMT), epithelial cells of solid tumours undergo cellular changes that enable them to escape their structural confines via increased mobility and invasiveness, to enter into the bloodstream, and to adhere to endothelial cells and give birth to distant metastases. Thus, tumour cells that have undergone EMT, and which are probably the most aggressive, are not detectable by the EpCAM targeting method. Alternatively, researchers have demonstrated the identification of CTCs utilizing the differences in their physical properties such as size and mass comparing to red blood cells with the aid of acoustic waves and microfluidic devices (Li, P. et al. *Proceedings of the National Academy of Sciences,* 2015, 112, 4970). However, this method may suffer from low specificity generating potential false positive or false negative results. In addition, the quantitative analysis of circulating tumour DNA (ctDNA) via real time PCR, may also be a feasible way to achieve similar goals than with the CTC detection (Alix-Panabières, C. et al. *Annual Review of Medicine,* 2012, 63, 199; Heitzer, E. et al. *Clinical Chemistry,* 2015, 61, 112). Nonetheless, within several hours of release of ctDNA, it is removed from the circulation by liver and kidneys. Moreover, ctDNA exists both in healthy people and cancer patients creating difficulties for setting the appropriate threshold.

Therefore, there is a high demand for the development of a more reliable and faster detection method for the identification of CTCs and/or TCs in patient body fluids.

SUMMARY OF THE INVENTION

In general, the invention relates to a method of detecting and/or quantifying the number of CTCs/TCs present in a given liquid biopsy comprising the significant steps of using a hyperoxic environment and a fluorophore-labelled metabolic indicator; and also to a specifically designed device for carrying out said method based on the use of microfluidic chips.

Thus, in a first aspect, the invention relates to an in vitro method (hereinafter referred to as "first method of the invention") for the detection of a circulating tumour cell (CTC) and/or a tumour cell (TC) in a liquid sample comprising the steps of:
   a) optionally, culturing the liquid sample in a cell culture medium;
   b) incubating the cells contained in the liquid sample or the cells obtained in step a) with a solution supplemented with a fluorophore-labelled metabolic indicator and saturated with oxygen, during an appropriate time to allow the CTCs/TCs to accumulate the fluorophore-labelled metabolic indicator;

c) removing the excess of the fluorophore-labelled metabolic indicator not accumulated in cells; and d) measuring the fluorescence of the fluorophore-stained cells wherein the detection of a fluorophore-stained cell having a fluorescence intensity superior to a control cell indicates the presence of a CTC/TC in the liquid sample.

In a second aspect, the invention relates to an in vitro method (hereinafter referred to as "second method of the invention") for diagnosing a tumour and/or metastasis in a subject comprising detecting the presence of a CTC/TC in a biofluid sample of said subject by the first method of the invention wherein if the presence of a CTC/TC in a biofluid sample of said subject is detected, then the subject suffers from a tumour and/or metastasis.

In a third aspect, the invention relates to an in vitro method (hereinafter referred to as "third method of the invention") for determining the prognosis or for monitoring the progression of a cancer and/or metastasis in a subject comprising detecting and quantifying the presence of a CTC/TC in a biofluid sample of said subject by the first method of the invention and comparing the number of CTCs/TCs in the biofluid sample of said subject with the number of CTCs/TCs in a reference sample obtained from the same subject at an earlier time of point of the disease wherein a decrease in the number of CTCs/TCs with respect to the same number in the reference sample is indicative that the subject has a good prognosis, or wherein an increase in the number of CTCs/TCs with respect to the same number in the reference sample is indicative that the subject has a poor prognosis.

In a fourth aspect, the invention relates to an in vitro method (hereinafter referred to as "fourth method of the invention") for monitoring the effectiveness of a therapy administered to a subject diagnosed with a cancer and/or metastasis or for designing a customized therapy for said subject comprising detecting and quantifying the presence of a CTC/TC in a biofluid sample of said subject before and after said therapy, by the first method of the invention wherein a decrease in the number of CTCs/TCs after the therapy administered with respect to the same number before the therapy is indicative that the therapy administered is effective, or wherein an increase or no change in the number of CTCs/TCs after the therapy administered with respect to the same number before the therapy is indicative that the therapy administered is ineffective or that the subject is in need of an alternative therapy.

In a fifth aspect, the invention relates to an in vitro method (hereinafter referred to as "fifth method of the invention") for the identification of compounds suitable for the treatment of cancer and/or metastasis comprising detecting and quantifying the presence of a CTC/TC in a biofluid sample of a subject suffering from cancer and/or metastasis that has been treated with a candidate compound by the first method of the invention wherein the compound is considered effective for the treatment of cancer and/or metastasis when the number of CTCs/TCs decreases with respect to the same number in a reference sample.

In a sixth aspect, the invention relates to an in vitro method (hereinafter referred to as "sixth method of the invention") for the identification of compounds capable of inducing cancer and/or metastasis comprising detecting and quantifying the presence of a CTC/TC in a biofluid sample of a subject which has been treated with a candidate compound by the first method of the invention wherein the compound is considered as capable of inducing cancer and/or metastasis when the number of CTCs/TCs increases with respect to the same number in a reference sample.

In another aspect, the invention relates to a device comprising a set of microfluidic chips for the detection of circulating tumour cells (CTCs) or tumour cells (TCs) in a liquid sample comprising:

a) a mixing chip comprising
  i. at least two inlets, wherein one inlet is for introducing the liquid sample and the other inlet(s) is/are for introducing a solution comprising a fluorophore-labelled metabolic indicator saturated with oxygen or components thereof, all the inlets converging in a micromixer for the mixture and incubation of the liquid sample and the solution comprising a fluorophore-labelled metabolic indicator saturated with oxygen, and
  ii. an outlet to allow the exit of the mixture to the purification chip;

b) a purification chip comprising
  i. an inlet for the entrance of the mixture,
  ii. a main microchannel with constrictions and lateral bifurcation microchannels for the extraction of the fluorophore-labelled metabolic indicator not accumulated in cells while avoiding the removal of cells,
  iii. a main microchannel outlet for the exit of cells to the detection chip, and
  iv. further lateral bifurcation outlets for the exit of the extracted fluorophore-labelled metabolic indicator; and c) a detection chip comprising three inlets, a first central inlet for the entrance of cells and the second and third inlets for the entrance of a solution for cell focusing, wherein the second and third inlets are situated at opposite sides of the first central inlet, all the inlets converging into a single microchannel which is optionally widen for being used as inspection region in the detection of stained cells by fluorescence, and an outlet for the exit of the mixture of cells and the solution.

In another aspect, the invention relates to a microfluidic chip selected from the group consisting of:

a) a mixing chip comprising
  (i) at least two inlets, wherein one inlet is for introducing a liquid sample and the other inlet(s) is/are for introducing a solution comprising a fluorophore-labelled metabolic indicator saturated with oxygen or components thereof, all the inlets converging in a micromixer for the mixture and incubation of the liquid sample and the solution comprising a fluorophore-labelled metabolic indicator saturated with oxygen, and
  (ii) an outlet to allow the exit of the mixture to a purification chip;

b) a purification chip comprising
  (i) an inlet for the entrance of a mixture,
  (ii) a main microchannel with constrictions and lateral bifurcation microchannels for the extraction of the fluorophore-labelled metabolic indicator not accumulated in cells while avoiding the removal of cells,
  (iii) a main microchannel outlet for the exit of cells to the detection chip, and
  (iv) further lateral bifurcation outlets for the exit of the extracted fluorophore-labelled metabolic indicator; and c) a detection chip comprising three inlets, a first central inlet for the entrance of cells and the second and third inlets for the entrance of a solution for cell focusing, wherein the second and third inlets are situated at opposite sides of the first central inlet, all the inlets converging into a single microchannel which is optionally widen for being used as inspection region in the detection of stained cells by fluorescence, and an outlet for the exit of the mixture of cells and the solution or a set of microfluidic chips consisting of at least two microfluidic chips selected from a), b) and c).

In another aspect, the invention relates to a kit comprising:

a) a set of microfluidic chips according to the invention and b) a fluorophore-labelled metabolic indicator.

In another aspect, the invention relates to the use of the device of the invention or of the microfluidic chip or set of microfluidic chips of the invention or kit of the invention for the detection and/or quantification of CTCs/TCs in a liquid sample.

In a further aspect, the invention relates to the use of the device of the invention or of the microfluidic chip or set of microfluidic chips of the invention or kit of the invention for CTCs/TCs sorting, isolating or capturing.

In a further aspect, the invention relates to the use of a fluorophore-labelled metabolic indicator for the detection and/or quantification of CTCs/TCs in a liquid sample.

DETAILED DESCRIPTION OF THE INVENTION

Figure 1:
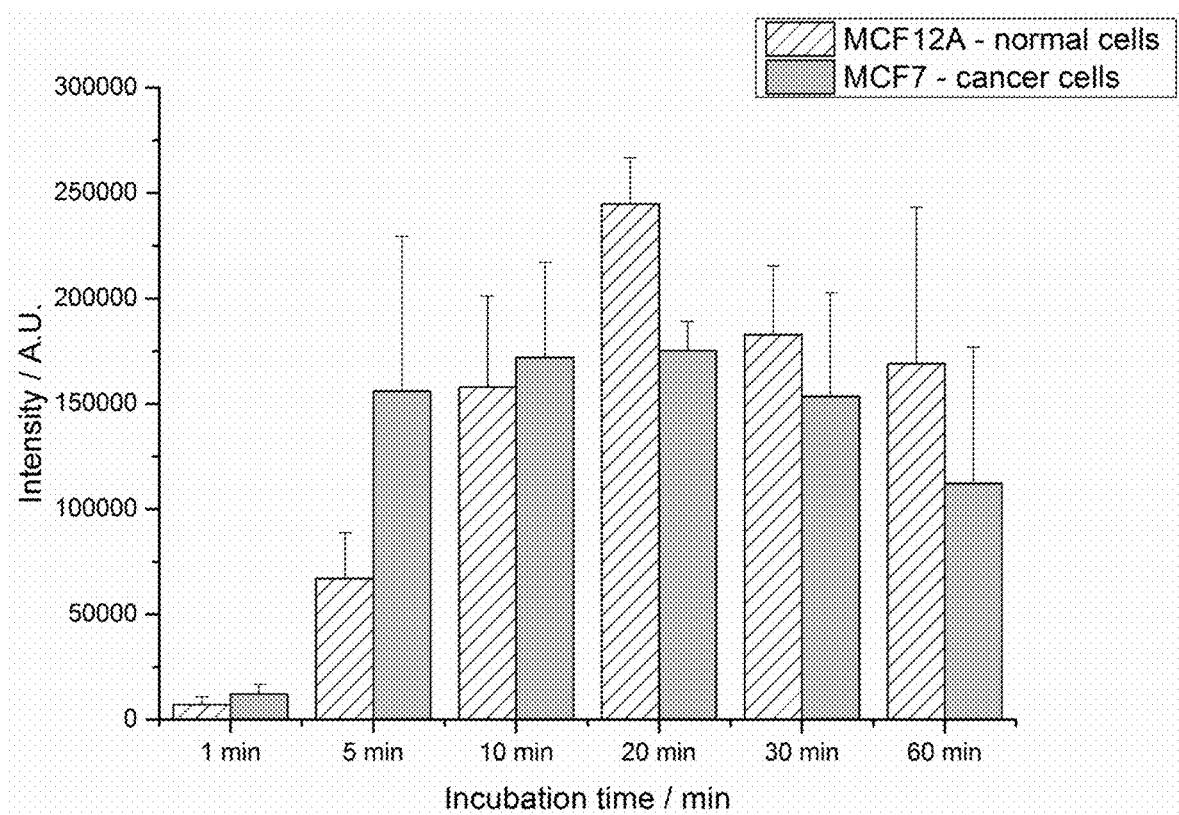
FIG. 1: Fluorescence intensities of 2-NBDG from normal and cancer cells at different incubation time points (1 minute, 5 minutes, 10 minutes, 20 minutes, 30 minutes and 60 minutes). 25 cells of each cell type were counted. A.U., arbitrary units.

This invention proposes a distinctive detection approach based on the differences in cell metabolism. Biomass and energy needs for cancer cells are met by aerobic or anaerobic glycolysis and not by oxidative phosphorylation. This is the Warburg effect which is the characteristic effect of the malignant cells. Cancer cells consume at least 10 times more glucose than healthy cells to meet increased bioenergetic and biomass demands for cell growth and proliferation. 2-Deoxy-D-glucose (2-DG) is a glucose analog with 2-hydroxyl groups replaced by hydrogen and it interrupts glycolysis and accumulates in the cytoplasm. 2-DG is uptaken by the glucose transporters of the cell. (Zhang, D. et al. *Cancer Letters*, 2014, 355, 176) Therefore, cancer cells with higher glucose uptake, have also a higher uptake of 2-DG. The inventors use fluorophore-labelled 2-DG (specifically 2-NBDG) as a metabolic indicator for the identification and/or quantification of circulating tumor cells (CTCs) and/or tumour cells (TCs) in the background of healthy cells based on the significant fluorescence intensity differences.

Previous researchers have shown that cancer cells altered glucose metabolism, which is significantly affected by the amount of dissolved oxygen (Zhang D. et al. Cancer Letters, 2014, 355:176). To this end, the culturing medium was replaced with the one containing excess amount of dissolved oxygen before incubating cells with 2-NBDG. Surprisingly, it turned out to work in a very convenient manner, showing relevant fluorescence intensity differences between the healthy and cancer cells in terms of the detection of CTC/TCs. Most cancer cells predominantly produce energy by a high rate of glycolysis followed by lactic acid fermentation in the cytosol, rather than by a comparatively low rate of glycolysis followed by oxidation of pyruvate in mitochondria as in most normal cells which is an oxygen-dependent process (Annibaldi, A. et al. *Current Opinion in Clinical Nutrition & Metabolic Care*, 2010, 13, 466). In the presence of excess amount of oxygen (hyperoxic environment), instead of fully respiring the adequate oxygen, cancer cells ferment, leading to the generation of a significantly higher glycolytic rate compared to those of their normal tissues of origin. (Annibaldi, A. et al. *Current Opinion in Clinical Nutrition & Metabolic Care*, 2010, 13, 466). This is known as the Warburg effect. This effect was discovered several decades ago. However, it is the first time to maximize the metabolic differences of cancerous and normal cells based on the Warburg effect for the detection of circulating tumour cells in body fluids.

Detection Method of the Invention

In a first aspect, the invention relates to an in vitro method (hereinafter referred to as "first method of the invention") for the detection of a circulating tumour cell (CTC) and/or a tumour cell (TC) in a liquid sample comprising the steps of:

a) optionally, culturing the liquid sample in a cell culture medium;
b) incubating the cells contained in the liquid sample or the cells obtained in step a) with a solution supplemented with a fluorophore-labelled metabolic indicator and saturated with oxygen, during an appropriate time to allow the CTCs/TCs to accumulate the fluorophore-labelled metabolic indicator;
c) removing the excess of the fluorophore-labelled metabolic indicator not accumulated in cells; and
d) measuring the fluorescence of the fluorophore-stained cells wherein the detection of a fluorophore-stained cell having a fluorescence intensity superior to a control cell indicates the presence of a CTC/TC in the liquid sample.

The first method of the invention allows the detection of circulating tumour cells (CTCs) and/or tumour cells (TCs) in a liquid sample.

The term "circulating tumour cell" or "CTC", as used herein, refers to a cell that has shed into the vasculature from a primary tumour and circulates in the bloodstream.

The term CTC, in the context of the present invention, also includes tumour cells in the peritoneal and lymphatic system. CTCs can be identified by methods well known by the person skilled in the art, for example by using specific antibodies able to recognize specific tumoral markers such as EpCAM, Her 2, CK19 or PSA.

The term "tumour cell" or "TC", as used herein, refers to a cell that can grow and divide at an unregulated, quick pace. TC can be identified by methods well known by the person skilled in the art, for example by using specific antibodies able to recognize specific tumoral markers such as EpCAM, Her 2, CK19 or PSA.

The expression "liquid sample", as used herein, refers to any kind of liquid sample that potentially contains TCs or CTCs. In a preferred embodiment, the liquid sample is a biofluid.

The term "biofluid" in the context of the present invention refers to any biological secretion or fluid, whether physiological or pathological, which is produced in the body of a subject. Such biofluids include, without limitation, blood, bronchoalveolar washing fluid, urine, nasal secretion, ear secretion, urethral secretion, cerebrospinal fluid, pleural fluid, synovial fluid, peritoneal fluid, ascites fluid, pericardial liquid, amniotic fluid, gastric juice, lymphatic fluid, interstitial fluid, saliva, sputum, liquid deposition, tears, mucus, sweat, milk, semen, vaginal secretions, fluid coming from ulcer, blisters, abscesses and other surface eruptions. Said samples can be obtained by conventional methods, using processes known in the state of art by the person skilled in the art, such as blood extraction, instillation and aspiration of liquid during bronchofibroscopy, cisternal, ventricular or lumbar puncture, pleural puncture or thoracocentesis, joint or synovial percutaneous puncture, abdominal puncture, amniocentesis, expectoration, peritoneal percutaneous puncture, pericardial percutaneous puncture, etc., or by simple harvesting. In a preferred embodiment the biofluid is blood, particulary whole blood. The blood sample is typically extracted by means of puncturing an artery or vein, normally a vein from the inner part of the elbow or from the back of the hand, the blood sample being collected in an air-tight vial or syringe. A capillary puncture normally on the heel or on the distal phalanxes of fingers can be performed for analysis by means of a micromethod. Typically when the liquid sample is blood, the first method of the invention detects CTC and when the liquid sample is other biofluid different from blood, the method detects TC.

Step (a) of the first method of the invention is optional, and comprises culturing the liquid sample in a cell culture medium and at the appropriate temperature. The conditions of the culture depend on the type of cells and are well known by the person skilled in the art. Typically, the sample is cultured in a humidified atmosphere and with an appropriate amount of $CO_2$. It is also possible that the sample is cultured in absence of $CO_2$, for example in a specific cell culture medium such as Leibovitz's L-15. Therefore, in a preferred embodiment, step (a) is carried out in a cell culture medium with 0-10% $CO_2$, typically with 4-10% $CO_2$, preferably with 5% $CO_2$.

The term "cell culture medium", as used herein, refers to any culture medium in which a TC or a CTC is capable of growing. Suitable culture media are standard media such as, without limitation, DMEM, EMEM, IMDM, RPMI-1640, GMEM, BME, MEM or Medium 199. The person skilled in the art knows the appropriate cell culture medium for culturing each type of cells. Preferably, low glucose or glucose free cell culture media is used, more preferably EMEM, preferably EMEM supplemented with 10% fetal bovine serum, 0.01 mg/mL human recombinant insulin and 2 mM L-glutamine and 1% penicillin-streptomycin. The cell culture medium can also be a medium having the standard amount of glucose or a medium having a high amount of glucose. In another embodiment the cell culture medium is a medium for supporting cell growth in a $CO_2$ free environment. The person skilled in the art knows that the incubation time needs to be adjusted depending on the amount of glucose contained in the medium.

In another embodiment the cell culture medium is DMEM, preferably DMEM/F-12 supplemented with 20 ng/mL of human epidermal growth factor, 100 ng/mL of cholera toxin, 0.01 mg/mL of bovine insulin, 500 ng/mL of hydrocortisone 95% and 5% donor horse serum.

Conditions for culturing the liquid sample are known by the skilled person, particularly it is cultured in a bottle, flask or plate placed in an incubator having a humidified atmosphere with an appropriate amount of $CO_2$ and at the appropriate temperature.

In an embodiment step a) is carried out in a humidified atmosphere. The expression "humidified atmosphere", as used herein, refers to the relative humidity of the incubator wherein the sample is cultured. Typically, a humidified atmosphere is an atmosphere having at least 80% relative humidity. This can be achieved by a specific incubator having devices for controlling humidity, $CO_2$, oxygen and temperature.

Step a) is carried out at an appropriate temperature to grow the cells that is well known by the person skilled in the art, preferably in a range comprised between 20° C. and 40° C., more preferably between 36° C. and 37° C., even more preferably at 37° C.

In a preferred embodiment, culturing the liquid sample is carried out for an appropriate amount of time, particularly overnight, more particularly 12 hours.

However, typically for clinical samples step (a) of the first method of the invention is not carried out, and the cells contained in the liquid sample are submitted directly to step (b). This can be done by incubating directly the liquid sample containing the cells or by isolating previously the cells from the original liquid sample and resuspending said cells in an appropriate medium or solution before the incubation. In a preferred embodiment the original liquid sample is used in step (b).

Step (b) of the first method of the invention comprises incubating the cells contained in the liquid sample or the cells obtained in step (a) with a solution supplemented with a fluorophore-labelled metabolic indicator and saturated with oxygen. If the liquid sample is not submitted to step a), typically the liquid sample can be directly submitted to step (b) or, optionally, the cells are isolated from the sample, for example by centrifugation or other means, and said cells are incubated with the solution supplemented with a fluorophore-labelled metabolic indicator and saturated with oxygen. On the other hand, is step (a) has been previously carried out, it is possible to proceed to step (b) without removing the cell culture medium used in step (a) and by adding the solution supplemented with a fluorophore-labelled metabolic indicator and saturated with oxygen to the culture resulting from step (a). Another option, if step (a) has been previously carried out, is removing the cell culture medium used in a) and replacing it with the solution used in step (b). The replacement of the cell culture medium is typically made by removing the original cell medium, optionally washing cells and adding in the solution supplemented with a fluorophore-labelled metabolic indicator and saturated with oxygen.

The expression "a solution supplemented with a fluorophore-labelled metabolic indicator" refers to a solution selected from the group consisting of a cell culture medium and a salt buffer solution. Any cell culture medium can be used. In a preferred embodiment the cell culture medium used in step (b) is the same culture medium used in step (a). Any salt buffer solution that does not damage the cells can be used, such as, preferably, any salt buffer solution selected from the group consisting of phosphate-buffered saline (PBS), trizma buffer, 4-(2-hydroxyethyl)-1-piperazineethanesulfonic acid (HEPES), 2-(N-morpholino)ethanesulfonic acid (MES), Tris buffer, 4-(N-morpholino)butanesulfonic acid (MOBS), sodium acetate, citric acid, and any combination thereof. More preferably the salt buffer solution is 1×PBS or HEPES.

The expression "saturated with oxygen" refers to a solution having a maximum amount of dissolved oxygen. The percentage of saturation refers to the amount of dissolved oxygen present to the maximum amount possible in water. When a volume of water at fixed temperature, salinity and pressure reaches equilibrium and is completely saturated with oxygen, it can be defined as containing 100% oxygen.

Typically, the fluorophore-labelled metabolic indicator is firstly dissolved in the solution and then supplied with oxygen to reach the dissolved oxygen saturation level. The oxygen sources may be oxygen bags or bottles.

Different ways of saturating a solution with oxygen may be used such as bubbling oxygen and adding chemicals (hydrogen peroxide, sodium percarbonate), etc. In a preferred embodiment, the solution supplemented with a fluorophore-labelled metabolic indicator is saturated with oxygen by bubbling the oxygen into said solution during an appropriate time. This time depends on the solution volume, temperature and oxygen flow. The saturation of the solution can be monitored by methods well known in the art, such as commercially available dissolved oxygen sensor kits. Preferably, the oxygen is bubbled during at least 1 minute, at least 5 minutes, at least 10 minutes, at least 20 minutes to reach the saturated condition.

The term "fluorophore-labelled metabolic indicator", as used herein, refers to a compound labelled with a fluorophore that is uptaken by a CTC/TC in a greater manner than by a normal cell due to the different metabolism of cancer cells. Suitable metabolic indicators for use in the invention are, without limitation, folates, amino acids, monosaccharides, lipids, glycolipids, chimeric antibodies, nanobodies, peptides, mono or oligo nucleotides and polysaccharides. Exemplary metabolic indicators for use in the invention are, without limitation, folinic acid (5-formyl-tetrahydrofolate), folic acid, glutamine, alfa-ketoglutarate, oxoglutarate, aspartate, N-acetyl-aspartate, acetylcholine, 2-hydroxyglutarate, pyruvate, alanine, glutamate, fructose, galactose, fructose-1-phosphate, cysteine, saccharose, calcium folinate and glycine. Said indicators are labelled with a fluorophore by methods well-known in the state of the art. In a preferred embodiment the fluorophore-labelled metabolic indicator is a fluorophore-labelled 2-D-glucose derivative. The expression "fluorophore-labelled 2-D-glucose derivative", as used herein, refers to a glucose analog that interrupts glycolysis and accumulates inside the cell. Examples of fluorophore-labelled 2-D-glucose derivatives are, without limitation, 2-NBDG, 6-NBDG, IRDye 800CW 2DG, Xenolight Redi-Ject 2-DG 750, CyNE 2-DG and Cy5.5-D-Glucosamine. In a more preferred embodiment, the fluorophore-labelled 2-D-glucose derivative is 2-(N-(7-Nitrobenz-2-oxa-1,3-diazol-4-yl)Amino)-2-Deoxyglucose (2-NBDG). 2-NBDG is a glucose analog with 2-hydroxyl group replaced by hydrogen having Formula (I).

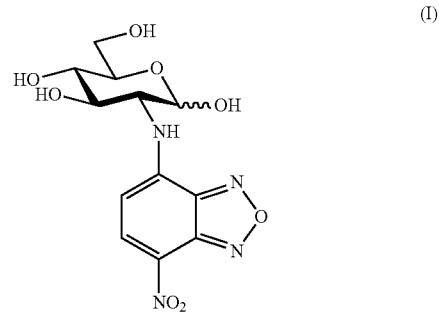

The incubation of step (b) is carried out in the same conditions as the incubation disclosed in step (a). All the embodiments disclosed for step (a) are also applicable to step (b). In a preferred embodiment the incubation is carried out in a humidified atmosphere. In another preferred embodiment the incubation is carried out with 0-10% $CO_2$, preferably with 4-10% $CO_2$, more preferably with 5% $CO_2$.

The incubation of step (b) is carried out at the appropriate temperature and during an appropriate time to allow the CTCs/TCs to accumulate the fluorophore-labelled metabolic indicator.

Step (b) is carried out at an appropriate temperature to grow the cells well known by the person skilled in the art, preferably in a range comprised between 20° C. and 40° C., more preferably between 36° C. and 37° C., even more preferably at 37° C.

The appropriate time of incubation in step (b) is at least 1 minute, at least 2 minutes, at least 3 minutes, at least 4 minutes, at least 5 minutes. In a more preferred embodiment the incubation time of step (b) is five minutes. In a preferred embodiment the incubation time is less than 30 minutes, less than 20 minutes, less than 10 minutes. In a preferred embodiment the incubation time is comprised between 4 and 10 minutes. In another embodiment the incubation time is comprised between 2 and 25 minutes.

Step (c) of the first method of the invention comprises removing the excess of the fluorophore-labelled metabolic indicator not accumulated in cells.

The expression "excess of the fluorophore-labelled metabolic indicator" refers to the fluorophore-labelled metabolic indicator present in the medium and that is not accumulated in cells. Said removal may be done, without limitation, by changing the cell culture medium; or by washing with a solution such as a buffer, a cell culture medium or water; or by the use of a microfluidic device as disclosed in the present invention.

The final step of the method of the invention (step d) comprises measuring the fluorescence of the fluorophore-stained cells by any fluorescence detection method.

The expression "fluorophore-stained cells", as used herein, refers to cells that have uptaken the fluorophore-labelled metabolic indicator that is accumulated in their cytoplasm or within membrane. The fluorophore-stained cells are both, CTC/TCs and healthy cells.

Fluorescence may be measured, without limitation, by a fluorometer, by fluorescence microscopy, by Raman spectroscopy or by flow cytometry. In a preferred embodiment, fluorescence microscopy is used.

As a result of this method, the detection of a fluorophore-stained cell having a fluorescence intensity superior to a control cell indicates the presence of a CTC/TC in the liquid sample.

The term "control cell", as used in the first method of the invention, refers to a healthy or normal cell (i.e. a cell that has not undergone a cancerous process). In a preferred embodiment the control cell is a healthy cell. The fluorescence intensity of the control cell can be a value obtained previously. The control cell can also be a healthy cell present in the same liquid sample that is analyzed in which case the fluorescence of the CTCs/TCs and the fluorescence of the control cells can be measured at the same time and a CTC/TC is detected when the fluorescence intensity of a cell is greater than that of the surrounded cells. Then, in a preferred embodiment the control cell is in the same liquid sample.

The inventors have also developed a device specifically adapted for carrying out the first method of the invention. Therefore, in a preferred embodiment the first method of the invention is carried out using the device of the invention.

Diagnostic Method of the Invention

In a second aspect, the invention relates to a method (hereinafter referred to as "second method of the invention") for diagnosing a tumour and/or metastasis in a subject comprising detecting the presence of a CTC/TC in a biofluid sample of said subject by the first method of the invention wherein if the presence of a CTC/TC in a biofluid sample of said subject is detected, then the subject suffers from a tumour and/or metastasis.

"Diagnosing", as used herein, refers to assessing the probability according to which a subject is suffering from a disease. As will be understood by those skilled in the art, such as assessment, although preferred to be, may usually not be correct for 100% of the subjects to be diagnosed. The term, however, requires that a statistically significant portion of subjects can be identified as suffering from the disease or as having a predisposition therefore. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, at least 95%. The p-values are, preferably, 0.2, 0.1, 0.05.

The term "tumour", as used herein, refers to an abnormal mass of tissue which may be solid or fluid-filled. The term tumour includes pre-malignant lesions such as dysplasia, metaplasia, aplasia and encapsulated tumours, and malignant tumours. In a preferred embodiment the tumour is a malignant tumour. However, in the context of this invention, the term "tumour" does not include benign tumours.

The term "metastasis" is understood as the distance propagation, fundamentally but not limited by the lymphatic, peritoneal or blood stream, of the cancer causing cells, and the growth of new tumours in the destination sites of said metastasis.

"Subject" in the present invention is understood as any animal classified as mammal and includes but is not limited to domestic and farm animals, primates and humans, for example human beings, non-human primates, cows, horses, pigs, sheep, goats, dogs, cats or rodents. Preferably, the subject is a female or male human being of any race or age. In the context of the present invention, the subject is a subject who potentially suffers from a tumour or has been previously diagnosed with cancer.

The terms "biofluid", "CTC" and "TC" have been defined previously in the context of the first method of the invention.

Prognostic Method of the Invention

In a third aspect, the invention relates to an in vitro method (hereinafter referred to as "third method of the invention") for determining the prognosis or for monitoring the progression of a cancer and/or metastasis in a subject comprising detecting and quantifying the presence of a CTC/TC in a biofluid sample of said subject by the first method of the invention and comparing the number of CTCs/TCs in the biofluid sample of said subject with the number of CTCs/TCs in a reference sample obtained from the same subject at an earlier time of point of the disease
  wherein a decrease in the number of CTCs/TCs with
    respect to the same number in the reference sample is
    indicative that the subject has a good prognosis, or
  wherein an increase in the number of CTCs/TCs with
    respect to the same number in the reference sample is
    indicative that the subject has a poor prognosis.

As used in the present invention, the expression "monitoring the progression", which is equivalent to "determining the prognosis", relates to the determination of one or several parameters indicating the progression of the disease in a patient diagnosed with cancer and/or metastasis. Parameters suitable for determining the evolution of a subject diagnosed with cancer and/or metastasis are selected from the group consisting of risk of relapse, disease-free survival and/or overall survival of the subject. As used herein, the expression "risk of relapse" is understood as the probability of a subject developing cancer or metastasis after a disease-free period; "disease-free survival" is understood as the time period after the treatment in which the cancer is not found; and "overall survival of the subject" is understood as the percentage of subjects who survive, from the time of the diagnosis or treatment, after a defined time period. The expression "cancer", as used herein, refers to a disease caused by a malignant tumour in which abnormal cells divide without control and can invade nearby tissues.

The term "reference sample", as used in the context of the third method of the invention, refers to a first sample obtained from the same subject at an earlier time of point of the disease.

The second sample is taken from the same subject having cancer from which the first measure is derived, at a second period of time, i.e., at any time after the first period of time, e.g., one day, one week, one month, two months, three months, 1 year, 2 years, or more after the first sample. In a particular embodiment, the first sample is taken prior to the subject receiving treatment, e.g. chemotherapy, radiation therapy, or surgery, and the second sample is taken after treatment. In another particular embodiment, the first sample is taken after the subject has started/received treatment, e.g. chemotherapy, radiation therapy, or surgery, and the second sample is taken later, at different time periods during a course of treatment. These methods allow for the evaluation of the progression of cancer in a selected subject previously diagnosed as suffering from cancer and/or metastasis. Consequently, if the cancer and/or metastasis has a poor prognosis, a further therapy should be designed to treat said disease in said subject. The progression of the cancer after said new treatment can be easily followed according to the teachings of this invention.

CTC/TCs can be quantified by counting the number of CTC/TCs detected by the first method of the invention in a liquid sample.

In the context of the present invention, a "decrease" in the number of CTCs/TCs with respect to the reference sample is understood as a variation in the number of CTCs/TCs under the reference sample of at least 0.9 times, 0.75 times, 0.2 times, 0.1 times, 0.05 times, 0.025 times, 0.02 times, 0.01 times, 0.005 times or even less compared to the reference sample.

In the context of the present invention, an "increase" in the number of CTCs/TCs with respect to the reference sample is understood as a variation in the number of CTCs/TCs above the reference sample of at least 1.1 times, 1.5 times, 5 times, 10 times, 20 times, 30 times, 40 times, 50 times, 60 times, 70 times, 80 times, 90 times, 100 times or even more times as compared to the reference sample.

Thus, a significant decrease in the number of CTCs/TCs with respect to the same number in the reference sample is indicative that the cancer is not in progression (i.e. the subject has a good prognosis). On the contrary, if a significant increase in the number of CTCs/TCs with respect to the same number in the reference sample is obtained, this is indicative that the cancer is in progression (i.e. the subject has a bad prognosis). Thus, the therapy administered to the subject under study should be changed and a new therapy should be designed to treat cancer.

The terms "metastasis", "subject", "CTC", "TC" and "biofluid" have been previously defined in the context of the first and second methods of the invention.

Method For Monitoring the Effectiveness of a Therapy

In a fourth aspect, the invention relates to an in vitro method (hereinafter referred to as "fourth method of the invention") for monitoring the effectiveness of a therapy administered to a subject diagnosed with a cancer and/or metastasis or for designing a customized therapy for said subject comprising detecting and quantifying the presence of a CTC/TC in a biofluid sample of said subject before and after said therapy, by the first method of the invention wherein a decrease in the number of CTCs/TCs after the therapy administered with respect to the same number before the therapy is indicative that the therapy administered is effective, or wherein an increase or no change in the number of CTCs/TCs after the therapy administered with respect to the same number before the therapy is indicative that the therapy administered is ineffective or that the subject is in need of an alternative therapy.

The expression "monitoring the effectiveness of a therapy", as used herein, refers to follow up the disease during a treatment to determine if said treatment is effective or not.

As used herein, the term "therapy" or "treatment" collectively refers to the means of any class, hygienic means, pharmacological means, surgical means or physical means, the purpose of which is to prevent and/or cure or relieve a disease or pathology or its symptoms. In cancer therapy, a variety of treatments can be used in an attempt to eliminate or contain the cancer. Treatment for cancer may involve active surveillance, hormonal therapy, radiation therapy, chemotherapy or some combination. In a specific case, said treatment is a pharmacological treatment, i.e., a treatment comprising the administration of a drug to a subject to prevent, relieve and/or cure a disease, e.g., cancer, or to relieve, reduce or eliminate one or more symptoms associated with said disease. Best decision is made depending on the stage of the disease.

Briefly, depending on several factors (e.g., age of the subject, as well as the size, location and cancer phase), (i) cytotoxic/cytostatic treatments, such as chemotherapy, which uses medicinal products against cancer to destroy the cancerous cells upon making the medicinal products circulate through the body through the blood vessels; radiotherapy, which uses high energy radiations to kill the cancer cells, and antitumor agents; and/or (ii) immunotherapy, wherein the administered compound stimulates, enhances or strengthens the natural function of the immune system against cancer to recognize and eliminate the cancerous cells from the body, can be used. Thus, the method of the invention allows determining the response of the subject having cancer to any treatment, particularly, to any cytotoxic and/or cytostatic treatment and, more specifically, to a treatment by means of chemotherapy, radiotherapy, antitumor agents or combinations thereof.

Suitable chemotherapy agents include but are not limited to alkylating agents [e.g., Cisplatin, Carboplatin, Oxaliplatin, BBR3464, Chlorambucil, Chlormethine, Cyclophosphamides, Ifosmade, Melphalan, Carmustine, Fotemustine, Lomustine, Streptozocin, Busulfan, Dacarbazine, Mechlorethamine, Procarbazine, Temozolomide, ThioTPA, Uramustine, etc.]; anti-metabolites [e.g., purine (azathioprine, mercaptopurine), pyrimidine (Capecitabine, Cytarabine, Fluorouracil, Gemcitabine), folic acid (Methotrexate, Pemetrexed, Raltitrexed), etc.]; vinca alkaloids [e.g., Vincristine, Vinblastine, Vinorelbine, Vindesine, etc.]; a taxane [e.g., paclitaxel, docetaxel, BMS-247550, etc.]; an anthracycline [e.g., Daunorubicin, Doxorubicin, Epirubicin, Idarubicin, Mitoxantrone, Valrubicin, Bleomycin, Hydroxyurea, Mitomycin, etc.]; a topoisomerase inhibitor [e.g., Topotecan, Irinotecan Etoposide, Teniposide, etc.]; a monoclonal antibody [e.g., Alemtuzumab, Bevacizumab, Cetuximab, Gemtuzumab, Panitumumab, Rituximab, Trastuzumab, etc.]); a photosensitizer [e.g., Aminolevulinic acid, Methyl aminolevulinate, Porfimer sodium, Verteporfin, etc.]; a tyrosine kinase inhibitor [e.g., Gleevec™]; an epidermal growth factor receptor inhibitor [e.g., Iressa™, erlotinib (Tarceva™), gefitinib, etc.]; an FPTase inhibitor [e.g., FTIs (RI 15777, SCH66336, L-778,123), etc.]; a KDR inhibitor [e.g., SU6668, PTK787, etc.]; a proteosome inhibitor [e.g., PS341, etc.]; a TS/DNA synthesis inhibitor [e.g., ZD9331, Raltirexed (ZD 1694, Tomudex), ZD9331, 5-FU, etc.]; an S-adenosyl-methionine decarboxylase inhibitor [e.g., SAM468A, etc.]; a DNA methylating agent [e.g., TMZ, etc.]; a DNA binding agent [e.g., PZA, etc.]; an agent which binds and inactivates $O^6$-alkylguanine AGT [e.g., BG]; a c-ra/-I antisense oligo-deoxynucleotide [e.g., ISIS-5132 (CGP-69846A)]; tumor immunotherapy; a steroidal and/or non-steroidal antiinflammatory agent [e.g., corticosteroids, COX-2 inhibitors]; or other agents such as Alitretinoin, Altretamine, Amsacrine, Anagrelide, Arsenic trioxide, Asparaginase, Bexarotene, Bortezomib, Celecoxib, Dasatinib, Denileukin Diftitox, Estramustine, Hydroxycarbamide, Imatinib, Pentostatin, Masoprocol, Mitotane, Pegaspargase, and Tretinoin. Suitable chemotherapy agents are described with more detail in the literature, such as in The Merck Index in CD-ROM, 13th edition.

This method allows for the evaluation of a particular treatment for a selected subject previously diagnosed with cancer and/or metastasis. Consequently, if the therapy is not efficacious for treating cancer in said subject, then said therapy should be changed and a new therapy should be designed to treat cancer in said subject. The course of the new treatment can be easily followed according to this method.

The terms "cancer", "metastasis", "subject", "CTC", "TC", "biofluid", "decrease" and "increase" have been previously defined in the context of the previous methods of the invention.

Methods For the Identification of Compounds of the Invention

Method for the identification of compounds suitable for the treatment of cancer and/or metastasis.

The first method of the invention can also be used for the screening for compounds suitable for the treatment of cancer and/or metastasis in a model of said disease.

In a fifth aspect, the invention relates to an in vitro method (hereinafter referred to as "fifth method of the invention") for the identification of compounds suitable for the treatment of cancer and/or metastasis comprising detecting and quantifying the presence of a CTC/TC in a biofluid sample of a subject suffering from cancer and/or metastasis that has been treated with a candidate compound by the first method of the invention wherein the compound is considered effective for the treatment of cancer and/or metastasis when the number of CTCs/TCs decreases with respect to the same number in a reference sample.

The term "reference sample", as used in respect of the fifth method of the invention, relates to either a sample derived from the subject wherein the therapy is being tested but obtained from the subject prior to the administration of the therapy or either a sample from a patient suffering from cancer which has been left untreated or which has been treated with a control therapy, preferably the same excipient, carrier or vehicle which is used in the candidate compound which is being screened.

The term "therapy", a used herein, encompasses the treatment of existing cancer as well as preventive treatment (i.e. prophylaxis).

In a preferred embodiment, the subject is not a human-being.

Example of suitable animals for use in the screening method of the invention include, but are not limited to, mice, rats, rabbits, monkeys, guinea pigs, dogs and cats. In accordance with this aspect, the test compound or a control compound is administered to a suitable animal and the effect on the levels of the number of CTCs is determined. Examples of agents include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art. Test compounds further include, for example, antibodies (e.g. polyclonal, monoclonal, humanized, anti-idiotypic, chimeric and single chain antibodies as well as Fab, F(ab')2, Fab expression library fragments, and epitope-binding fragments of antibodies). Further agents or libraries of compounds may be presented, for example, in solution, on beads, chips, bacteria, spores, plasmids or phage.

If the compound is a low-molecular weight compound, then this can be generated by various methods known to the art, preferably synthetically, in particular by combinatorial chemistry, or by biochemical methods, in particular by recombinant expression or purification from biological probes. The compound is of low molecular weight ("small molecules") or the library is composed of molecules with low molecular weight ("small molecule library"). A "small molecule" is defined as a complex collection of compounds, which are produced in a non-biological way that means which are not produced by recombinant expression, like for instance most protein or peptide libraries. "Small molecules" can be generated by various methods known to the art, but are preferably produced by synthetically, more preferably by combinatorial chemistry, to generate a compound library with a maximum chemical diversity within the constraints of predicted attractive drug characteristics. If the compound to be assayed for its suitability for the treatment of cancer and/or metastasis is a peptide or a peptide library, then these can be generated by various methods known to the art for their use as candidate compounds, but they are preferably produced by biochemical methods, more preferably by recombinant expression in prokaryotic or eukaryotic cells.

The compound to be tested for its suitability for the therapy of cancer and/or metastasis can be formulated with a pharmaceutically acceptable carrier to produce a pharmaceutical composition, which can be administered to a human or other animal. A pharmaceutically-acceptable carrier can be, for example, water, sodium phosphate buffer, phosphate-buffered saline, normal saline or Ringer's solution or other physiologically-buffered saline, or other solvent or vehicle such as a glycol, glycerol, an oil such as olive oil or an injectable organic ester. A pharmaceutically acceptable carrier can also contain physiologically acceptable compounds that act, for example, to stabilize or increase the absorption of the modulatory compound. One skilled in the art would know that the choice of a pharmaceutically acceptable carrier, including a physiologically acceptable compound, depends, for example, on the route of administration of the composition.

The terms "cancer", "metastasis", "CTC", "TC", "biofluid" and "decrease" have been previously defined in the context of the previous aspects.

Method for the identification of compounds capable of inducing cancer and/or metastasis in a subject In a sixth aspect, the invention relates to an in vitro method (hereinafter referred to as "sixth method of the invention") for the identification of compounds capable of inducing cancer and/or metastasis comprising detecting and quantifying the presence of a CTC/TC in a biofluid sample of a subject which has been treated with a candidate compound by the first method of the invention wherein the compound is considered as capable of inducing cancer and/or metastasis when the number of CTCs/TCs increases with respect to the same number in a reference sample.

The term "reference sample", as used in respect of the sixth method of the invention, relates to either a sample derived from the subject wherein the effect of a candidate compound is tested obtained prior to the administration of the candidate compound or to either a sample from a patient suffering from cancer which has been left untreated or which has been treated with a control therapy, preferably the same excipient, carrier or vehicle which is used in the candidate compound which is being screened.

In a preferred embodiment, the subject is not a human-being. Suitable animals that can be used have been described in the context of the fifth method of the invention. Other terms have been previously defined.

Apparatus of the Invention

The assay was then implemented into a continuous flow system for the analysis of CTCs in patient bloodstream or for the analysis of TCs on other liquid samples.

Miniaturization and automation of the whole assay to obtain an autonomous dedicated device can provide numerous advantages such as the possibility of performing in-situ measurements, thus being feasible to provide information to the patient faster than using the conventional methods. Moreover, these systems normally reduce the overall costs, since they do not require specialized personnel, improve safety to the users, and minimize human errors. In terms of the identification of CTCs/TCs, a device comprising, but not limited to, three different microfluidic chips was conceived: one for the mixing of cells with the fluorophore-labelled metabolic indicator, one for the purification of cells from the excess of fluorophore-labelled metabolic indicator, and another one for the continuous detection of single cells.

In another aspect, the invention relates to a device comprising a set of microfluidic chips for the detection of circulating tumour cells (CTCs) and/or tumour cells (TCs) in a liquid sample comprising:
a) a mixing chip comprising
  i. at least two inlets, wherein one inlet is for introducing the liquid sample and the other inlet(s) is/are for introducing a solution comprising a fluorophore-labelled metabolic indicator saturated with oxygen or components thereof, all the inlets converging in a micromixer for the mixture and incubation of the liquid sample and the solution comprising a fluorophore-labelled metabolic indicator saturated with oxygen, and
  ii. an outlet to allow the exit of the mixture to the purification chip;
b) a purification chip comprising
  i. an inlet for the entrance of the mixture,
  ii. a main microchannel with constrictions and lateral bifurcation microchannels for the extraction of the fluorophore-labelled metabolic indicator not accumulated in cells while avoiding the removal of cells,
  iii. a main microchannel outlet for the exit of cells to the detection chip, and
  iv. further lateral bifurcation outlets for the exit of the extracted fluorophore-labelled metabolic indicator; and
c) a detection chip comprising three inlets, a first central inlet for the entrance of cells and the second and third inlets for the entrance of a solution for cell focusing, wherein the second and third inlets are situated at opposite sides of the first central inlet, all the inlets converging into a single microchannel which is optionally widen for being used as inspection region in the detection of stained cells by fluorescence, and an outlet for the exit of the mixture of cells and the solution.

The device of the invention can also comprise more than three different microfluidic chips.

The terms "device" and "apparatus" are used herein interchangeably. The device of the invention comprises a set of microfluidic chips. The expression "microfluidic chip", as used herein, refers to a system in which low volumes of fluids are processed to achieve multiplexing, automation and high-throughput screening. In a preferred embodiment, the microfluidic chips are fabricated with a polymeric material. The term "polymeric material", as used herein, refers to any organic compound, natural or synthetic, with high molecular weight made of repetitive structural units, preferably to elastomer and thermoplastic polymers. Exemplary polymeric materials that can be used for the present invention are, without limitation, polydimethylsiloxane (PDMS), poly (methylmethacrylate) (PMMA), polycarbonate (PC), poly (ethylene terephthalate) glycol (PETG), polyethylene (branched) (LDPE), polystryrene (PS), polypropylene (PP), polyetheretherketone (PEEK), polyethylene terephthalate (PET), polyethylene (PE), polyvinylidene chloride (PVDC), polyvinyl chloride (PVC), polysulfone (PSU), cyclic olefin polymer (COP) and cyclic olefin copolymer (COC). In a preferred embodiment the polymeric material is polydimethylsiloxane (PDMS), preferably PDMS sealed with glass.

First, a mixing chip is used. The expression "mixing chip", as used herein, refers to a chip with a micromixer which permits an efficient mixture of reagents in a short time, specifically the incubation of cells with the fluorophore-labelled metabolic indicator. Said chip has, but not limited to, two inlets (one for introducing the liquid sample and the other for introducing a solution comprising a fluorophore-labelled metabolic indicator saturated with oxygen). Therefore, in a preferred embodiment, the mixing chip has two inlets: one for introducing the liquid sample and the other for introducing a solution comprising a fluorophore-labelled metabolic indicator saturated with oxygen. The mixing chip may have additional inlets in order to provide separately the different components of the solution, for example, an inlet for oxygen supplying and/or inlets for the fluorophore-labelled metabolic indicator to accommodate the final user's needs.

The liquid sample that enters the mixing chip can be the original liquid sample obtained, for example, from a biological fluid, or it can be a liquid sample obtained after isolating the cells of the original liquid sample and resuspending them in a suitable cell culture medium or in a buffer solution.

All the inlets of the mixing chip converge in a micromixer. The term "micromixer", as used herein, refers to a microchannel designed for improving mixture between liquids and wherein the liquid sample is incubated with the fluorophore-labelled metabolic indicator. Exemplary micromixers useful for the invention are known by the person skilled in the art and can be, without limitation, a two-dimensional T-shape micromixer, a serpentine or a two-split micromixer.

Experimental conditions were optimized to promote fluorophore-labelled metabolic indicator cellular uptake in the mixing chip. In a preferred embodiment, the micromixer has between 1 and 2000 μm width, more preferably between 10 and 2000 μm width; more preferably between 100 and 1000 μm width; preferably between 200 and 500 μm width; even more preferably 250 μm-width. In a preferred embodiment, the micromixer has 250 μm-width and 75 μm-depth.

The mixing chip also has an outlet to allow the exit of the mixture to the purification chip.

In a preferred embodiment the total volume of the mixing chip is comprised between 0.1 and 5000 μl.

Then, a purification chip was used to remove the excess of fluorophore-labelled metabolic indicator which was not accumulated by cells.

The expression "purification chip", as used herein, refers to a chip based on a main microchannel where different constrictions and lateral bifurcation microchannels were intercalated. This design allows the elimination of the fluorophore-labelled metabolic indicator through the lateral channels with a minimal loss of cells. Said purification chip has an inlet for the entrance of the mixture coming from the mixing chip and several outlets. Preferably, the purification chip has three outlets: a main microchannel outlet for the exit of cells to the detection chip, and two further lateral bifurcation outlets for the exit of the extracted fluorophore-labelled metabolic indicator. In a preferred embodiment, the main microchannel has a width comprised between 10 and 2000 μm; preferably between 100 and 1000 μm; more preferably between 150 and 500 μm; the most preferred 170 μm.

In an embodiment, the purification chip includes lateral bifurcation microchannels on one/both sides of the main microchannel, conforming at least 90° with the flow direction of the main microchannel, from which the fluorophore-labelled metabolic indicator is removed. In a preferred embodiment, between 1 and 20 lateral bifurcation microchannels are located on the sides of the main microchannel. In a preferred embodiment, the purification chip includes lateral bifurcation microchannels on both sides of the main microchannel, from which the fluorophore-labelled metabolic indicator is removed. Preferably, five lateral bifurcation microchannels are located on each side of the main microchannel. In another embodiment, each lateral bifurcation microchannel has a width comprised between 1 and 2000 μm. Ideally, the width of each lateral bifurcation microchannel should be between 1 and 100 μm to avoid the entrance of cells; preferably between 25 and 100 μm; more preferably between 50 and 100 μm; more preferably between 75 and 100 μm; even more preferably 75 μm.

In another preferred embodiment, the main microchannel has constrictions before each lateral bifurcation microchannel to minimize the entrance of cells into these lateral bifurcation microchannels, each constriction placed on the opposite side of said lateral bifurcation microchannel. Preferably, each constriction before each lateral bifurcation microchannel has a width that is 2 to 10 times thinner than the width of the main microchannel. Ideally, each constriction is between 1 and 1000 μm-width, preferably between 1 and 200 μm-width, preferably between 10 and 100 μm-width; preferably between 25 and 75 μm-width; more preferably between 50 and 75 μm-width; even more preferably 65 μm-width.

The purification chip can include pillars of different size and shape for acting as a filter of cell sorting. Said pillars could be, without limitation, cylinder-, cube- or rhombus-shaped, among others. The dimensions of said pillars are preferably between 1-1000 μm for width and length, and between 1 and 2000 μm-depth.

Figure 7:
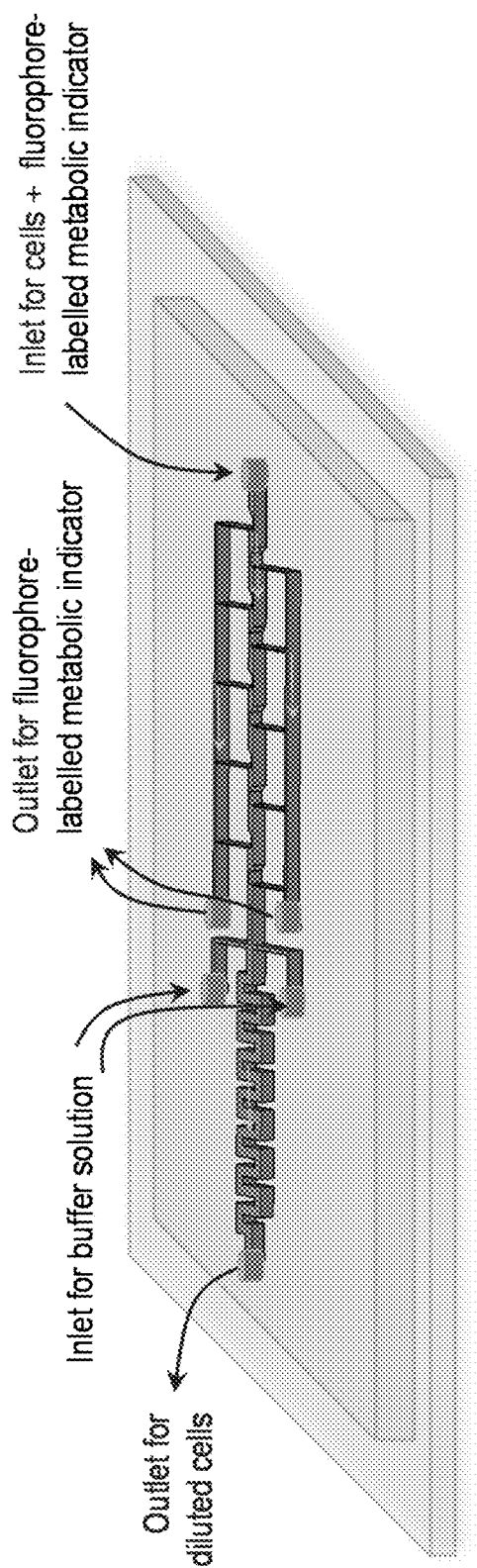
FIG. 7: Schematic representation of an embodiment of a purification chip design wherein additional inlets and microchannels for diluting the sample with buffer solution have been added.

In another embodiment the purification chip also comprises additional inlets and microchannels for diluting the sample, particularly for diluting the fluorophore-labelled metabolic indicator that remains after cell concentration. Said additional inlets are inlets for the entry of liquid such as buffer solution, cell culture media or water, preferably buffer solution. Said additional microchannels can be added along the whole main microchannel or at the end of all lateral bifurcation microchannels (i.e. at the end of the main microchannel). FIG. 7 shows an embodiment of said purification chip. In an embodiment of the invention the configuration of the purification chip is the configuration shown on FIG. 7.

In an embodiment, the depth of the purification chip is comprised between 0.1 and 5 mm. In a preferred embodiment the depth of the purification chip is comprised between 1 and 2000 μm; preferably between 1 and 1000 μm; more preferably between 1 and 500 μm; more preferably between 25 and 100 μm; even more preferably between 50 and 90 μm; even more preferably 75 μm.

Preferably, the total volume of the purification chip is comprised between 0.1 and 5000 μL.

In a preferred embodiment the configuration of the purification chip is the configuration shown on FIG. 6b.

Once cells were purified, the detection of tumour cells was performed in the detection chip, which was based on the hydrodynamic focusing technique. This technique allows the pass of single cells through a small width section (such as in flow cytometers), thus permitting measuring single cell fluorescence from the hypermetabolic tumour cells. In an embodiment the detection chip is based on the hydrodynamic focusing of cells. The expression "detection chip", as used herein, relates to a chip based on a single microchannel which is preferably widen for being used as inspection region in the detection of stained cells by fluorescence. In an embodiment, the single microchannel of the detection chip has a width comprised between 1 and 2000 μm; preferably between 10 and 2000 μm; preferably between 10 and 1000 μm; more preferably between 10 and 500 μm; more preferably between 10 and 100 μm; even more preferably between 25 and 90 μm; even more preferably between 50 and 80 μm; even more preferably between 55 and 75 μm; preferably 60 μm. In another embodiment, the inspection region has a width comprised between 10 and 2000 μm; preferably between 50 and 1000 μm; more preferably between 100 and 800 μm; even more preferably between 400 and 700 μm; most preferably 600 μm.

Said detection chip has at least three inlets: a first central inlet for the entrance of concentrated cells and the other two inlets for the entrance of a solution for cell focusing. For single cell detection, cells should be centered in the single microchannel. Therefore, the second and third inlets are situated at opposite sides of the first central inlet. In a preferred embodiment, the flow rate of the solution acting as sheath flow in the detection chip is the same or higher than the flow rate of cells, preferably is at least two times larger compared to the flow rate of concentrated cells; even more preferably the flow rate of the solution is comprised between 0.005 and 50 mL/h; preferably 0.075 mL/h and the flow rate of cells is comprised between 0.005 and 50 mL/h; preferably 0.025 mL/h.

All the inlets converge into a single microchannel. The single microchannel can have the same width along it since it is not necessary to widen that microchannel for detection. However, it is preferable that the single microchannel has a widen region for being used as inspection region in the detection of stained cells by fluorescence. This widen region reduces the cell passing velocity in favour of detection. In a preferred embodiment, the inspection region of the detection chip is from 2 to 15-fold wider than the single microchannel of the detection chip.

The detection chip has also an outlet for the exit of the mixture of cells and the solution for cell focusing.

Additional inlets and channels can be potentially added to the design of the detection chip to achieve a 3D flow focusing.

Preferably, the solution for cell focusing is selected from the group consisting of a cell culture medium, a buffer solution and water. In a preferred embodiment said solution is a buffer, more preferably phosphate-buffered saline (PBS).

In an embodiment, the depth of the detection chip is comprised between 0.1 and 5 mm. In a preferred embodiment, the depth of the detection chip is comprised between 1 and 2000 µm; preferably between 10 and 2000 µm; more preferably between 10 and 500 µm; more preferably between 10 and 100 µm; more preferably between 25 and 100 pm; even more preferably between 50 and 100 µm; preferably 75 µm.

In a preferred embodiment the total volume of the detection chip is comprised between 0.1 and 5000 µl.

Preferably, the microchannels and/or micromixer of the device have between 1 and 2000 µm-width and between 1 and 2000 µm-depth.

In another embodiment, the device further comprises a set of pumps and/or a detection system for fluorescence measurements and/or a microscope coupled to the chips. The set of pumps and detection system have also all the necessary electronic and fluidic connections with the other components of the device. In a preferred embodiment, the detection system for fluorescence measurements has been coupled to the inspection region of the detection chip.

The terms "CTCs", "TCs", "liquid sample", "solution comprising a fluorophore-labelled metabolic indicator" and "saturated with oxygen" have been defined in the context of the previous aspects of the invention. All the embodiments previously disclosed are applicable to this aspect of the invention.

Microfluidic Chips of the Invention

The set of microfluidic chips that form the device can be disposable and the invention is also directed to a mixing chip, a purification chip, a detection chip or a combination of at least two of said chips.

In another aspect, the invention relates to a microfluidic chip selected from the group consisting of:
  a) a mixing chip comprising
    (i) at least two inlets, wherein one inlet is for introducing a liquid sample and the other inlet(s) is/are for introducing a solution comprising a fluorophore-labelled metabolic indicator saturated with oxygen or components thereof, all the inlets converging in a micromixer for the mixture and incubation of the liquid sample and the solution comprising a fluorophore-labelled metabolic indicator saturated with oxygen, and
    (ii) an outlet to allow the exit of the mixture to a purification chip;
  b) a purification chip comprising
    (i) an inlet for the entrance of a mixture,
    (ii) a main microchannel with constrictions and lateral bifurcation microchannels for the extraction of the fluorophore-labelled metabolic indicator not accumulated in cells while avoiding the removal of cells,
    (iii) a main microchannel outlet for the exit of cells to the detection chip, and
    (iv) further lateral bifurcation outlets for the exit of the extracted fluorophore-labelled metabolic indicator; and
  c) a detection chip comprising three inlets, a first central inlet for the entrance of cells and the second and third inlets for the entrance of a solution for cell focusing, wherein the second and third inlets are situated at opposite sides of the first central inlet, all the inlets converging into a single microchannel which is optionally widen for being used as inspection region in the detection of stained cells by fluorescence, and an outlet for the exit of the mixture of cells and the solution or a set of microfluidic chips consisting of at least two microfluidic chips selected from a), b) and c).

All the embodiments disclosed in the context of the apparatus of the invention are also applicable to the microfluidic chips of the invention.

Kits of the Invention

The invention also provides kits for carrying out the method of the invention.

In an aspect, the invention relates to a kit comprising:
  a) a set of microfluidic chips according to the invention and
  b) a fluorophore-labelled metabolic indicator.

Preferably the set of microfluidic chips comprises a mixing chip, a purification chip and a detection chip.

Preferably, the fluorophore-labelled metabolic indicator is a fluorophore-labelled 2-D-glucose derivative, more preferably 2-(N-(7-Nitrobenz-2-oxa-1,3-diazol-4-yl)Amino)-2-Deoxyglucose (2-NBDG).

In an embodiment, the kit further comprises at least a solution selected from the group consisting of a buffer solution, a cell culture medium and water. Preferably the buffer solution is PBS.

In another embodiment, the kit further comprises an oxygen source. Exemplary oxygen sources may be oxygen bottles or oxygen bags.

The terms "microfluidic chips", "fluorophore-labelled metabolic indicator", "fluorophore-labelled 2-D-glucose derivative", "buffer solution" and "cell culture medium" have been previously defined.

All the embodiments disclosed in the context of the previous aspects of the invention are also applicable to the kits of the invention.

Uses of the Invention

The device of the invention has application in liquid biopsy.

In an aspect, the invention relates to the use of the device of the invention, or to the use of the microfluidic chip or set of microfluidic chips of the invention, or to the use of the kit of the invention for the detection and/or quantification of CTCs/TCs in a liquid sample.

In a preferred embodiment, the flow rate of the solution for cell focusing in the detection chip is the same or higher than the flow rate of cells. Preferably, the flow rate of the solution for cell focusing is between 0.005 and 50 mL/h and the flow rate of cells is between 0.005 and 50 mL/h.

In another embodiment, the solution for cell focusing in the detection chip is selected from the group consisting of a cell culture medium, a buffer solution and water. In a more preferred embodiment the solution is a buffer solution, preferably selected from the group consisting of phosphate-buffered saline (PBS), trizma buffer, 4-(2-hydroxyethyl)-1-piperazineethanesulfonic acid (HEPES), 2-(N-morpholino)ethanesulfonic acid (MES), Tris buffer, 4-(N-morpholino)butanesulfonic acid (MOBS), sodium acetate, citric acid, and any combination thereof. In another preferred embodiment, the solution for cell focusing is a cell culture medium, preferably selected from the group consisting of DMEM, EMEM, IMDM, RPMI-1640, GMEM, BME, MEM and Medium 199.

In another embodiment the fluorophore-labelled metabolic indicator is a fluorophore-labelled 2-D-glucose derivative, preferably 2-NBDG.

In an embodiment, the detection and/or quantification of CTC/TCs is carried out by fluorescence, preferably by the first method of the invention.

In another embodiment, the mixture recirculates for the purification chip, preferably recirculates at least two times for the purification chip.

The device preserves cell viability for further analysis and CTCs/TCs from the liquid sample can be isolated by the method of the invention.

In another aspect, the invention relates to the use of the device of the invention, the use of the microfluidic chip or set of microfluidic chips of the invention, or the use of the kit of the invention for CTCs/TCs sorting, isolating or capturing.

In another aspect, the invention relates to the use of a fluorophore-labelled metabolic indicator for the detection and/or quantification of CTCs/TCs in a liquid sample, preferably a fluorophore-labelled 2-D-glucose derivative, more preferably 2-(N-(7-Nitrobenz-2-oxa-1,3-diazol-4-yl) Amino)-2-Deoxyglucose (2-N BDG).

All the embodiments disclosed in the context of the previous aspects can also be applied to the uses of the invention.

The invention is described below by means of the following examples which are merely illustrative and by no means limiting for the scope of the invention.

The present invention is also directed to:

[1]. An in vitro method for the detection of a circulating tumour cell (CTC) and/or a tumour cell (TC) in a liquid sample comprising the steps of:
   a) optionally, culturing the liquid sample in a cell culture medium;
   b) incubating the cells contained in the liquid sample or the cells obtained in step a) with a solution supplemented with a fluorophore-labelled metabolic indicator and saturated with oxygen, and during an appropriate time to allow the CTCs/TCs to accumulate the fluorophore-labelled metabolic indicator;
   c) removing the excess of the fluorophore-labelled metabolic indicator not accumulated in cells; and
   d) measuring the fluorescence of the fluorophore-stained cells
   wherein the detection of a fluorophore-stained cell having a fluorescence intensity superior to a control cell indicates the presence of a CTC/TC in the liquid sample.

[2]. The method according to [1], wherein the fluorophore-labelled metabolic indicator is a fluorophore-labelled 2-D-glucose derivative.

[3]. The method according to [2], wherein the fluorophore-labelled 2-D-glucose derivative is 2-(N-(7-Nitrobenz-2-oxa-1,3-diazol-4-yl)Amino)-2-Deoxyglucose (2-NBDG).

[4]. The method according to any of [1] to [3], wherein the solution supplemented with a fluorophore-labelled metabolic indicator and saturated with oxygen used in step b) is selected from the group consisting of a cell culture medium and a salt buffer solution.

[5]. The method according to any of [1] to [4], wherein the solution supplemented with a fluorophore-labelled metabolic indicator is saturated with oxygen by bubbling the oxygen into said solution.

[6]. The method according to any of [1] to [5], wherein step a) and/or step b) is carried out at a range of temperature comprised between 36° C. and 37° C.

[7]. The method according to any of [1] to [6], wherein the incubation time of step b) is at least 1 minute.

[8]. The method according to [7], wherein the incubation time of step b) is five minutes.

[9]. The method according to any of [1] to [8], wherein the liquid sample is a biofluid.

[10]. The method according to [9], wherein the biofluid is whole blood.

[11]. The method according to any of [1] to [10], wherein the control cell is a healthy cell.

[12]. The method according to any of [1] to [11], wherein the control cell is in the same liquid sample.

[13]. The method according to any of [1] to [12], which is carried out using the device of any of [19] to [21] or [23] to [40], or the microfluidic chip or set of microfluidic chips of any of [22] to [40], or the kit of any of [41] to [45].

[14]. An in vitro method for diagnosing a tumour and/or metastasis in a subject comprising detecting the presence of a CTC/TC in a biofluid sample of said subject by a method according to any of [1] to [13] wherein if the presence of a CTC/TC in a biofluid sample of said subject is detected, then the subject suffers from a tumour and/or metastasis.

[15]. An in vitro method for determining the prognosis or for monitoring the progression of a cancer and/or metastasis in a subject comprising detecting and quantifying the presence of a CTC/TC in a biofluid sample of said subject by a method according to any of [1] to [13] and comparing the number of CTCs/TCs in the biofluid sample of said subject with the number of CTCs/TCs in a reference sample obtained from the same subject at an earlier time of point of the disease wherein a decrease in the number of CTCs/TCs with respect to the same number in the reference sample is indicative that the subject has a good prognosis, or wherein an increase in the number of CTCs/TCs with respect to the same number in the reference sample is indicative that the subject has a poor prognosis.

[16]. An in vitro method for monitoring the effectiveness of a therapy administered to a subject diagnosed with a cancer and/or metastasis or for designing a customized therapy for said subject comprising detecting and quantifying the presence of a CTC/TC in a biofluid sample of said subject before and after said therapy, by a method according to any of [1] to [13]
   wherein a decrease in the number of CTCs/TCs after the therapy administered with respect to the same number before the therapy is indicative that the therapy administered is effective, or
   wherein an increase or no change in the number of CTCs/TCs after the therapy administered with respect to the same number before the therapy is indicative that the therapy administered is ineffective or that the subject is in need of an alternative therapy.

[17]. An in vitro method for the identification of compounds suitable for the treatment of cancer and/or metastasis comprising detecting and quantifying the presence of a CTC/TC in a biofluid sample of a subject suffering from cancer and/or metastasis that has been treated with a candidate compound by a method according to any of [1] to [13] wherein the compound is considered effective for the treatment of cancer and/or metastasis when the number of CTCs/TCs decreases with respect to the same number in a reference sample.

[18]. An in vitro method for the identification of compounds capable of inducing cancer and/or metastasis comprising detecting and quantifying the presence of a CTC/TC in a biofluid sample of a subject which has been treated with a candidate compound by a method according to any of [1] to [13] wherein the compound is considered as capable of inducing cancer and/or metastasis when the number of CTCs/TCs increases with respect to the same number in a reference sample.

[19]. A device comprising a set of microfluidic chips for the detection of circulating tumour cells (CTCs) and/or tumour cells (TCs) in a liquid sample comprising:
  a) a mixing chip comprising
    i. at least two inlets, wherein one inlet is for introducing the liquid sample and the other inlet(s) is/are for introducing a solution comprising a fluorophore-labelled metabolic indicator saturated with oxygen or components thereof, all the inlets converging in a micromixer for the mixture and incubation of the liquid sample and the solution comprising a fluorophore-labelled metabolic indicator saturated with oxygen, and
    ii. an outlet to allow the exit of the mixture to the purification chip;
  b) a purification chip comprising
    i. an inlet for the entrance of the mixture,
    ii. a main microchannel with constrictions and lateral bifurcation microchannels for the extraction of the fluorophore-labelled metabolic indicator not accumulated in cells while avoiding the removal of cells,
    iii. a main microchannel outlet for the exit of cells to the detection chip, and
    iv. further lateral bifurcation outlets for the exit of the extracted fluorophore-labelled metabolic indicator; and
  c) a detection chip comprising three inlets, a first central inlet for the entrance of cells and the second and third inlets for the entrance of a solution for cell focusing, wherein the second and third inlets are situated at opposite sides of the first central inlet, all the inlets converging into a single microchannel which is optionally widen for being used as inspection region in the detection of stained cells by fluorescence, and an outlet for the exit of the mixture of cells and the solution.

[20]. The device according to [19], further comprising a set of pumps and/or a detection system for fluorescence measurements and/or a microscope coupled to the chips.

[21]. The device according to [20], wherein the detection system for fluorescence measurements has been coupled to the inspection region of the detection chip.

[22]. A microfluidic chip selected from the group consisting of:
  a) a mixing chip comprising
    (i) at least two inlets, wherein one inlet is for introducing a liquid sample and the other inlet(s) is/are for introducing a solution comprising a fluorophore-labelled metabolic indicator saturated with oxygen or components thereof, all the inlets converging in a micromixer for the mixture and incubation of the liquid sample and the solution comprising a fluorophore-labelled metabolic indicator saturated with oxygen, and
    (ii) an outlet to allow the exit of the mixture to a purification chip;
  b) a purification chip comprising
    (i) an inlet for the entrance of a mixture,
    (ii) a main microchannel with constrictions and lateral bifurcation microchannels for the extraction of the fluorophore-labelled metabolic indicator not accumulated in cells while avoiding the removal of cells,
    (iii) a main microchannel outlet for the exit of cells to the detection chip, and
    (iv) further lateral bifurcation outlets for the exit of the extracted fluorophore-labelled metabolic indicator; and
  c) a detection chip comprising three inlets, a first central inlet for the entrance of cells and the second and third inlets for the entrance of a solution for cell focusing, wherein the second and third inlets are situated at opposite sides of the first central inlet, all the inlets converging into a single microchannel which is optionally widen for being used as inspection region in the detection of stained cells by fluorescence, and an outlet for the exit of the mixture of cells and the solution or a set of microfluidic chips consisting of at least two microfluidic chips selected from a), b) and c).

[23]. The device according to any of [19] to [21], or the microfluidic chip or set of microfluidic chips according to [22], wherein the microfluidic chips are fabricated with a polymeric material.

[24]. The device or the microfluidic chip or set of microfluidic chips according to [23], wherein the polymeric material is polydimethylsiloxane (PDMS).

[25]. The device according to any of [19] to [21] or [23] to [24], or the microfluidic chip or set of microfluidic chips according to any of [22] to [24], wherein the microchannels and/or micromixer have between 1 and 2000 μm-width and between 1 and 2000 μm-depth.

[26]. The device or the microfluidic chip or set of microfluidic chips according to [25], wherein the micromixer has 250 μm-width and 75 μm-depth.

[27]. The device according to any of [19] to [21] or [23] to [26], or the microfluidic chip or set of microfluidic chips according to any of [22] to [26], wherein the total volume of the mixing chip and/or the total volume of the purification chip and/or the total volume of the detection chip is comprised between 0.1 and 5000 μL.

[28]. The device according to any of [19] to [21] or [23] to [27], or the microfluidic chip or set of microfluidic chips according to any of [22] to [27], wherein the purification chip includes lateral bifurcation microchannels on one/both sides of the main microchannel, conforming at least 90° with the flow direction of the main microchannel, from which the fluorophore-labelled metabolic indicator is removed.

[29]. The device or microfluidic chip or set of microfluidic chips according to [28], wherein between 1 and 20 lateral bifurcation microchannels are located on the sides of the main microchannel.

[30]. The device or microfluidic chip or set of microfluidic chips according to [29], wherein five lateral bifurcation microchannels are located on each side of the main microchannel.

[31]. The device or microfluidic chip or set of microfluidic chips according to [30], wherein each lateral bifurcation microchannel has a width comprised between 1 and 100 μm.

[32]. The device according to any of [19] to [21] or [23] to [31], or the microfluidic chip or set of microfluidic chips according to any of [22] to [31], wherein the main microchannel has constrictions before each lateral bifurcation microchannel, each constriction placed on the opposite side of said lateral bifurcation microchannel to minimize the entrance of cells into these lateral bifurcation microchannels.

[33]. The device or the microfluidic chip or set of microfluidic chips according to [32], wherein each constriction before each lateral bifurcation microchannel has a width that is 2 to 10 times thinner than the width of the main microchannel.

[34]. The device according to any of [19] to [21] or [23] to [33], or the microfluidic chip or set of microfluidic chips according to any of [22] to [33], wherein the purification chip includes pillars of different size and shape for acting as a filter of cell sorting.

[35]. The device according to any of [19] to [21] or [23] to [34], or the microfluidic chip or set of microfluidic chips according to any of [22] to [34], wherein the purification chip comprises additional inlets and microchannels for diluting the sample.

[36]. The device according to any of [19] to [21] or [23] to [35], or the microfluidic chip or set of microfluidic chips according to any of [22] to [35], wherein the depth of the purification chip is comprised between 0.1 and 5 mm.

[37]. The device according to any of [19] to [21] or [23] to [36], or the microfluidic chip or set of microfluidic chips according to any of [22] to [36], wherein the detection chip is based on the hydrodynamic focusing of cells.

[38]. The device according to any of [19] to [21] or [23] to [37], or the microfluidic chip or set of microfluidic chips according to any of [22] to [37], wherein the single microchannel of the detection chip has a width between 10 and 10000 μm.

[39]. The device according to any of [19] to [21] or [23] to [38], or the microfluidic chip or set of microfluidic chips according to any of [22] to [38], wherein the inspection region of the detection chip is from 2 to 15-fold wider than the single microchannel of the detection chip.

[40]. The device according to any of [19] to [21] or [23] to [39], or the microfluidic chip or set of microfluidic chips according to any of [22] to [39], wherein the depth of the detection chip is comprised between 0.1 and 5 mm.

[41]. A kit comprising:
a) a set of microfluidic chips according to any of [22] to [40]; and
b) a fluorophore-labelled metabolic indicator

[42]. The kit according to [41], wherein the kit further comprises at least a solution selected from the group consisting of a buffer solution, a cell culture medium and water.

[43]. The kit according to any of [41] or [42], wherein the fluorophore-labelled metabolic indicator is a fluorophore-labelled 2-D-glucose derivative.

[44]. The kit according to [43], wherein the fluorophore-labelled 2-D-glucose derivative is 2-(N-(7-Nitrobenz-2-oxa-1,3-diazol-4-yl)Amino)-2-Deoxyglucose (2-NBDG).

[45]. The kit according to any of [41] to [44], wherein the kit further comprises an oxygen source.

[46]. Use of the device according to any of [19] to [21] or [23] to [40], or the microfluidic chip or set of microfluidic chips according to any of [22] to [40], or the kit according to any of [41] to [45] for the detection and/or quantification of CTCs/TCs in a liquid sample.

[47]. The use according to [46], wherein the flow rate of the solution for cell focusing in the detection chip is the same or higher than the flow rate of cells.

[48]. The use according to [47], wherein the flow rate of the solution for cell focusing is between 0.005 and 50 mL/h and the flow rate of cells is between 0.005 and 50 mL/h.

[49]. The use according to any of [46] to [48], wherein the solution for cell focusing in the detection chip is selected from the group consisting of a cell culture medium, a buffer solution and water.

[50]. The use according to [49], wherein the solution for cell focusing is a buffer solution.

[51]. The use according to [50], wherein the buffer solution is selected from the group consisting of phosphate-buffered saline (PBS), trizma buffer, 4-(2-hydroxyethyl)-1-piperazineethanesulfonic acid (HEPES), 2-(N-morpholino)ethanesulfonic acid (MES), Tris buffer, 4-(N-morpholino)butanesulfonic acid (MOBS), sodium acetate, citric acid, and any combination thereof.

[52]. The use according to [49], wherein the solution for cell focusing is a cell culture medium.

[53]. The use according to [52], wherein the cell culture medium is selected from the group consisting of DMEM, EMEM, IMDM, RPMI-1640, GMEM, BME, MEM and Medium 199.

[54]. The use according to any of [46] to [53], wherein the fluorophore-labelled metabolic indicator is a fluorophore-labelled 2-D-glucose derivative.

[55]. The use according to [54], wherein the fluorophore-labelled 2-D-glucose derivative is 2-(N-(7-Nitrobenz-2-oxa-1,3-diazol-4-yl)Amino)-2-Deoxyglucose (2-NBDG).

[56]. The use according to any of [46] to [55], wherein the detection and/or quantification of CTCs/TCs is carried out by fluorescence.

[57]. The use according to any of [46] to [56], wherein the detection and/or quantification is carried out by the method according to any of [1] to [13].

[58]. The use according to any of [46] to [57], wherein the mixture recirculates for the purification chip.

[59]. Use of the device according to any of [19] to [21] or [23] to [40], or the microfluidic chip or set of microfluidic chips according to any of [22] to [40], or the kit according to any of [41] to [45] for CTCs/TCs sorting, isolating or capturing.

[60]. Use of a fluorophore-labelled metabolic indicator for the detection and/or quantification of CTCs/TCs in a liquid sample.

[61]. Use according to [60], wherein the fluorophore-labelled metabolic indicator is a fluorophore-labelled 2-D-glucose derivative.

[62]. Use according to [61], wherein the fluorophore-labelled 2-D-glucose derivative is 2-(N-(7-Nitrobenz-2-oxa-1,3-diazol-4-yl)Amino)-2-Deoxyglucose (2-NBDG).

EXAMPLES

Materials and Methods

CdSe Qdot Functionalization

CdSe Qdot 625 ITK (purchased from Molecular Probes, Life Technologies) and 685 carboxyl quantum dots were functionalized with amino-polyethylene glycol (amino-PEG) 5000 MW through 1-ethyl-3-(3-dimethylaminopropyl) carbodiimide (EDC) coupling, to increase their biocompatibility. 1 μM of each Qdot was dispersed in 10 mM of MES (2-(N-morpholino)ethanesulfonic acid) buffer solution (pH=6.0) and amino-PEG was added with a molar ratio 1 (quantum dots):100 (amino-PEG). EDC was added based on a molar ratio 1:1, and the reaction was left for 2 h. Afterwards, solution was centrifuged using an ultrafiltration unit to remove big aggregates at 13,000 rpm for 20 min, and the sediment inside the ultrafiltration unit was collected by a reverse centrifugation at 2,000 rpm for 3 min. Functionalization of the quantum dots was checked by the evaluation of their stability under higher ionic strength solvents, using fluorimeter.

Cell Culture

MCF12A, a breast mammary epithelia-derived cell line, and MCF7 breast cancer cell line (American Type Culture Collection, ATCC, Manassas, Va., USA), were routinely cultured in DMEM/F-12 supplemented with 20 ng/mL of human epidermal growth factor, 100 ng/mL of cholera toxin, 0.01 mg/mL of bovine insulin, 500 ng/mL of hydrocortisone 95% and 5% donor horse serum; and in EMEM (Eagle's Minimum Essential Medium) supplemented with 10% fetal bovine serum, 0.01 mg/mL human recombinant insulin, 2 mM of L-glutamine and 1% Penicillin-Streptomycin, respectively. Each cell line was cultured in a humidified atmosphere with 5% $CO_2$ at 37° C.

Cell Labeling With Qdot@amino-PEG

To successfully identify different cell types in a cell mixture, previously functionalized Qdot 625 and 685 were used as the intracellular trackers for MCF12A and MCF7 cells, respectively. 50,000 cells/wells of each type were cultured separately onto glass cover slips inside 12-well plates and left growing for 48 h, at 5% $CO_2$ and 37° C. Then, cells were washed with pre-warmed 1×PBS for 1 minute and 100 nM of each Qdot@amino-PEG was added in the cell growth media, and waited for 1 hour. After the incubation, cells were washed 3 times with 1×PBS. MCF7 (Qdot685 labelled) cells were detached from the surface using Trypsin-EDTA solution 0.25% and re-cultured onto MCF12A (Qdot625 labelled) cells. Co-cultured cells were left for re-attaching for 12 h, with 5% $CO_2$ at 37° C.

2-NBD Glucose Uptake Measurements on Fixed Cells

To study the general uptake and retention of glucose, cells were exposed to 300 µM of 2-(N-(7-Nitrobenz-2-oxa-1,3-diazol-4-yl)Amino)-2-Deoxyglucose (2-NBDG) for different incubation times: 1, 5, 10, 20, 30, and 60 min. To achieve higher 2-NBDG accumulation inside MCF7 cells, cells were exposed to different conditions based on the concentrations of dissolved oxygen. The effects on oxygen availability were evaluated by exposing cells to the hyperoxic or hypoxic environment, created by bubbling 2-NBDG incubation media for 20 min with oxygen or nitrogen, respectively. Afterwards, cells were fixed with 4% paraformaldehyde solution in 1×PBS, for 20 min, and then washed 6 times with 1×PBS and mounted onto glass slides with Fluoromount G (Southern Biotech), for the fluorescence measurements.

2-NBD Glucose Uptake Measurements in Co-Cultured Cells

Co-cultured MCF7 (Qdot685 labelled) cells with MCF12A (Qdot625 labelled) cells were exposed to 300 µM of 2-NBDG for 5 min, under the hyperoxic environment, determined by the previous optimizations. Afterwards, cells were fixed with 4% paraformaldehyde solution in 1×PBS for 20 min, and then washed 6 times with 1×PBS and mounted onto glass slides with Fluoromount G (Southern Biotech), for the fluorescence measurements.

Fabrication of Microfluidic Chips

Three different microfluidic chips (mixing, purification and detection chips) were fabricated with polydimethylsiloxane (PDMS), sealed with glass.

Masters for moulding were fabricated using standard photolithography techniques. Thus, Si wafers were cleaned by sonication with acetone and isopropanol, dried in a stream of nitrogen, and subsequently heated at 110° C. in an oven for 2 h. A thin layer of negative photoresist (SU-8 2100) was spin-coated onto the surface of the silicon substrates at 100 rpm/s to 500 rpm for 10 s, followed by 300 rpm/s to 500 rpm for 30 s, and finally 10 s of 500 rpm/s to 300 rpm (total spinning time 50 s). A 10-minute soft-bake of the photoresist at 72° C. on a hot plate was followed. Then, high-resolution transparency photomasks were placed over the spin-coated resins and were exposed to UV-light at a dose of 40 mW/cm$^2$ for 4 s. After a post-exposure bake of 5 min at 72° C., the substrates were rinsed with SU-8 developer (1-methoxy-2-propanol acetate) and isopropanol to remove the unexposed photoresist. Masters were dried in a stream of nitrogen.

PDMS was mixed with curing agent (10:1) and poured onto the master moulds. Once degassed in vacuum, the mixture was cured at 80° C. for 15 minutes. Then, the PDMS layers were peeled off from the masters, and inlet/outlet holes were punched with a 1.25 mm-sized biopsy punch. Glass slides were used to seal the bottom of the PDMS layers. Then, both PDMS and glass slides were exposed to oxygen plasma treatment (100 W, 3% $O_2$, 0.2 mbar, 40 s) (Plasma Flecto 10, Plasma technology GmbH) for increasing their adhesion and were immediately bonded. Inlets and outlets were connected to syringes and waste containers, respectively, via polytetrafluoroethylene (PTFE) tubes (i.d. 0.8 mm).

For their evaluation, the constructed microfluidic chips were placed onto the translation stage of a conventional microscope (Motic BA310) or an epi-fluorescence microscope (NIKON TE2000E). Before all experiments, the chips were flushed with ethanol to remove all bubbles and thereafter with filtered PBS to condition the microchannels. In all microfluidic experiments, healthy and cancer cells were cultured separately using the previously optimized conditions. For purification and detection experiments, cells were incubated with 150 µM of 2-NBDG, since this concentration allows a clear visibility on the fluorescence images.

2-NBDG Glucose Uptake Measurements Within a Microfluidic Chip

For the incubation of cells with 2-NBDG within a microfluidic chip, MCF7 cells were detached from culture flasks, centrifuged at 1,300 rpm for 5 min and resuspended in 1 mL of 1×PBS under hyperoxic conditions. Then, 3 mL of the suspended cells and 3 mL of 150 µM 2-NBDG were placed in two syringes, which were located on a double channel syringe pump for their injection in the microfluidic chip at a flow rate of 0.025 mL/h. The mixing chip consisted of two different inlets for reagents (cells and 2-NBDG), which converged in a two-dimensional micromixer of 250 µm-width and 75 µm-depth (FIG. 5a). An outlet channel allowed the exit of the mixed solution. The total volume of the device was ~5 µL. An epi-fluorescence microscope was used to evaluate the response of the microsystem.

Cells Purification Within a Microfluidic Chip

Figure 6:
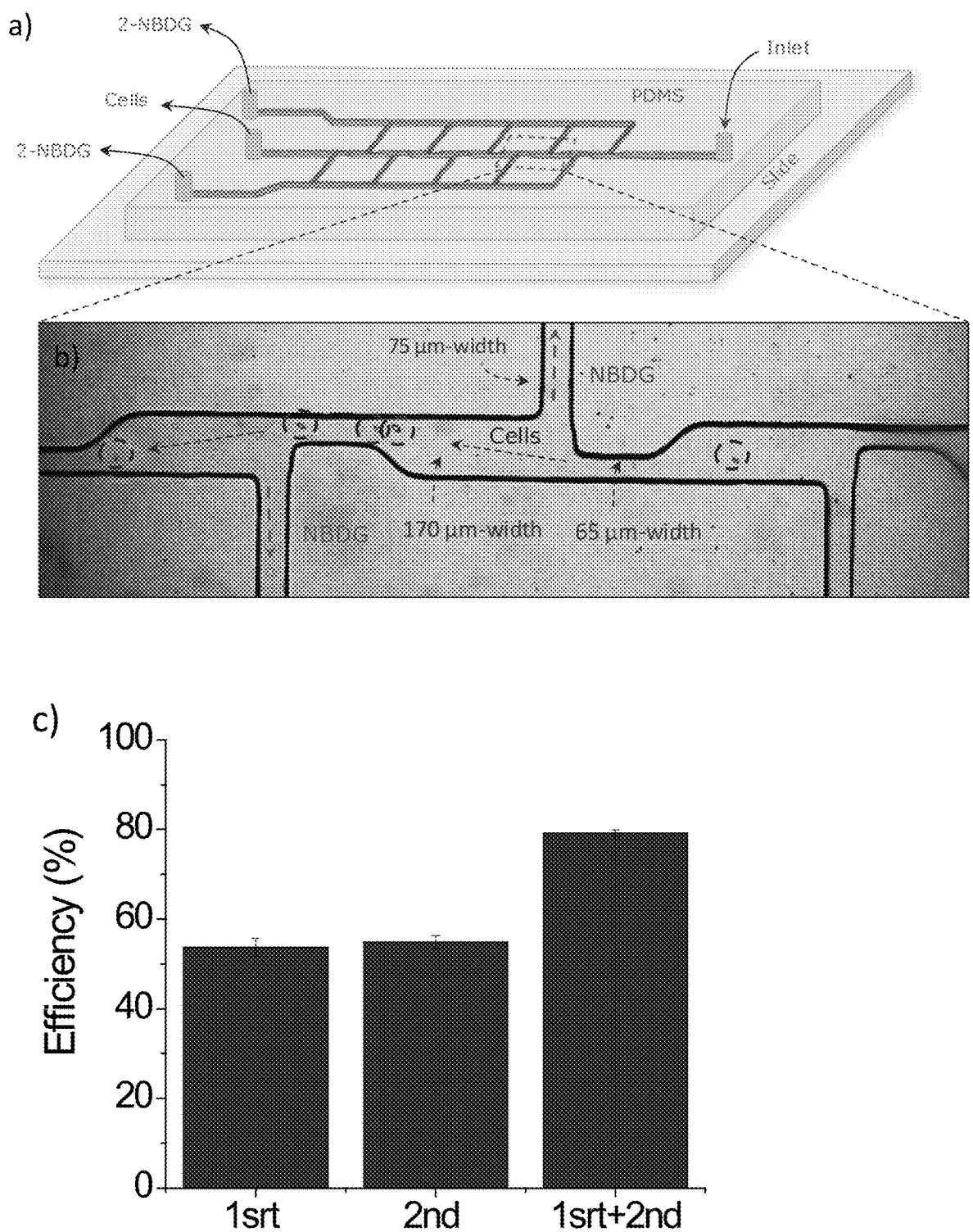
FIG. 6: a) Schematic representation of the purification chip design. b) Image from an amplified area of the microsystem, where the preferential linear movement of cells can be observed. c) Efficiency of the purification process for cancer cells. PDMS, polydimethylsiloxane; 1srt, first recirculation; 2nd, second recirculation.

A purification microfluidic chip was used to remove the excess of 2-NBDG, which was not uptaken by cells. The chip consisted of four connections: an inlet for the entrance of the solution (cells and 2-NBDG), an outlet for the collection of concentrated cells, and two more outlets for the extracted fluorophore. Five microchannels (75 µm-width) were located on each side of a central main channel (170 µm-width), which had a constriction before each bifurcation channel (65 µm-width) to avoid the entrance of cells on the lateral ones. The depth of the whole chip was 75 µm (FIG. 6).

To test the feasibility of the purification chip, a 5 mL solution containing MCF7 cells and 2-NBDG was prepared. Thus, MCF7 cells were detached from culture flasks, centrifuged at 1,300 rpm for 5 min and resuspended in 1 mL of 1×PBS under hyperoxic conditions. 2-NBDG was added (150 µM as final concentration) and the mixture was incubated for 5 min. Afterwards, 2-fold volume of the pre-cooled 1×PBS was added to stop the incubation. The suspended cells and 2-NBDG solution was pumped to the chip by means of a syringe pump at a flow rate of 0.8 mL/h. A conventional microscope was used to evaluate the response.

On-Line Monitoring of CTCs in a Microfluidic Chip

Figure 8:
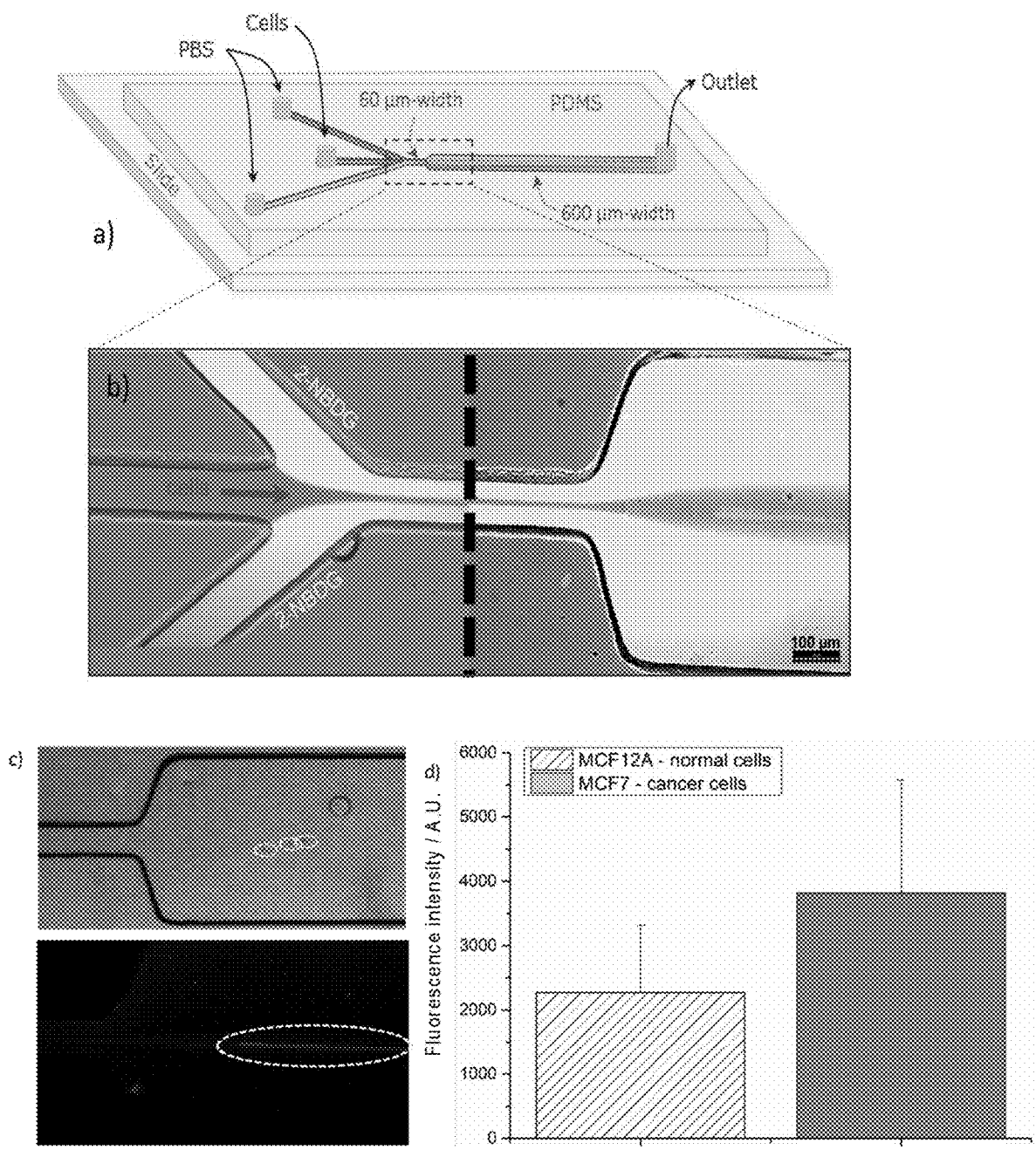
FIG. 8: a) Schematic representation of the detection chip. b) Proof of concept image of the hydrodynamic focusing design wherein the 2-NBDG solution has been used instead of PBS to make the flow focusing visible. The 2-NBDG solution is shown by the greater brightness, which acts as sheath flow. Cells pointed by an arrow are focused into the centre of the microchannel (white light and epi-fluorescence merged images from two different photographs) c) White light (top) and epi-fluorescence (bottom) images from the detection of cancer cells wherein buffer has been pumped through the lateral channels and cells are positioned at the middle of the single microchannel. Dashed circles highlight the presence of cells. 100 µm, scale bar. d) Quantification of the fluorescence intensity from the cancer and the healthy cells.

A detection chip based on the hydrodynamic focusing technique was constructed to continuously detect hypermetabolic cancer cells by measuring single cell fluorescence. It consisted of three inlets, a main single channel and an outlet (FIG. 8a). All inlet channels converged in a single one of 75 µm-width, which was widen to 600 µm (detection region). The conformation of the inlet channels ensures the focus of cells into a line, which can be further detected one by one. Depth of the whole microfluidic chip was 75 µm.

In order to check the correct function of the hydrodynamic focusing, MCF7 cells were stained with a fluorophore. 1×10$^6$ cultured MCF7 were washed with 1×PBS and 80 µg/mL of wheat germ agglutinin AlexaFluor555 conjugate were added to stain cell cytoskeleton, for 30 min at room temperature. After staining, cells were washed three times with 1×PBS to remove unbound molecules. Then, cells were detached from culture flask and centrifuged once at 1,300 rpm for 5 min. Stained cells were resuspended in 1×PBS as solvent to run the microfluidic device. Stained cells were pumped to the microsystem at 0.05 mL/h into the central channel, while 2-NBDG flowed at 0.1 mL/h through the lateral ones. 2-NBDG fluorescence was collected using an epi-fluorescence microscope with 465/95 excitation and 515/555 emission filters and AlexaFluor555 with 540/25 excitation and 605/55 emission filters.

For the on-line detection of cancer and healthy cells, MCF12A and MCF7 cells were separately detached from culture flasks, centrifuged at 1,300 rpm for 5 min and resuspended in 1 mL of 1×PBS under hyperoxic conditions. As mentioned above, hyperoxia was achieved by bubbling oxygen into the PBS solution for 20 min. 2-NBDG was then added to achieve 150 µM as the final concentration and incubated with suspended cells for 5 min, as the optimal condition. Afterwards, incubation was stopped by adding 2-fold volume of pre-cooled 1×PBS and non-uptaken 2-NBDG was removed by centrifuging cells at 1,300 rpm for 5 min and suspending in 1×PBS. The pre-labelled cells were injected into the central inlet channel of the microfluidic chip at a flow rate of 0.025 mL/h, while 1×PBS was pumped through the lateral ones at 0.075 mL/h. Single and double channel syringe pumps were used for pumping pre-labelled cells and PBS, respectively. An epi-fluorescence microscope was used to collect the fluorescence of the 2-NBDG uptaken by single cells (both, MCF12A and MCF7). Data was analyzed with Image J software.

Fluorescence Microscopy Analysis

Fixed cells were imaged with fluorescence microscopy and then analysed using Image J. Epi-fluorescence microscope NIKON TE2000E equipped with the 465/495 excitation and 515/555 emission filters was used to collect the fluorescence of 2-NBDG. Laser confocal scanning microscope equipped with 488, 543 and 633 nm lasers and 515/30, 590/50 and 650LP filters was used to image Qdot 625 and 685 nm.

Results

Example 1

Determination of Time of Exposure to 2-NBDG 2-(N-(7-Nitrobenz-2-oxa-1,3-diazol-4-yl)Amino)-2-Deoxyglucose (2-NBDG) is chosen as the model metabolism indicator. Healthy breast cells (MCF12A) and breast cancer cells (MCF7) were cultured separately to achieve a similar confluency before being incubated with 300 µM of 2-NBDG. The concentration of 2-NBDG was determined based on the gain of clear visibility on the fluorescence images. The fluorescence intensity was quantified using Image J. The same thresholds were set for fluorescence images of both healthy and cancer cells to remove the background noises. Any fluorescence intensities below the thresholds were discarded.

Cell metabolism can be regulated through the changes of its microenvironment. Therefore, to achieve maximum differentiation between the cancer and healthy cells, several parameters were optimized. Healthy and cancer cells were incubated with 2-NBDG for different time ranging from 1 to 60 min. As shown in FIG. 1, at the very beginning (1 min), cancer and healthy cells generate similar fluorescence intensities probably due to the physical absorption. With the increase of incubation time, cancer cells show higher fluorescence compared to healthy cells at 5 min. Interestingly, the fluorescence from healthy cells overtakes the cancer cells by further increasing the incubation time. Unlike glucose, 2-DG cannot undergo a further glycolysis inside cells thus replacing glucose with 2-DG hampers cell growth. Compared with healthy cells, cancer cells consume more glucose as well as its analog (2-DG) under the same circumstance. Hence, fluorescence intensities of both cancer and healthy cells increase at the beginning with cancer cells showing a greater acceleration. 2-NBDG has been found to be decomposed to a non-fluorescent derivative after entering into cells. Thus, the fluorescence intensity should reflect a dynamic equilibrium of generation and decomposition of 2-NBDG and the fluorescent metabolite. Moreover, when the accumulated 2-NBDG reaches a significant amount inside cancer cells, it inhibits their further growth and generates the cytotoxic effect. These synergic effects lead to the intensity decrease at the later stage. In addition, there is a metabolic lag between healthy and cancer cells, which might explain that the fluorescence from healthy cells overtakes cancer cells at the later time points. Therefore, the 2-NBDG incubation time is fixed at 5 min for the following optimizations.

Example 2

Determination of the Microenvironment Regarding Amount of Oxygen

Previous researches have shown that cancer cells altered glucose metabolism, which is significantly affected by the amount of dissolved oxygen. To this end, cell media were replaced with the ones bubbled with oxygen or nitrogen to simulate the hyperoxic and hypoxic microenvironment during the 5 min incubation time. As shown clearly in FIG. 2, in the case of hyperoxia, the fluorescence intensity gap between cancer and healthy cells is further enlarged compared to the control and hypoxia environments. This can be explained by the Warburg effect that in the presence of excess amount of dissolved oxygen, cancer cells ferment glucose into lactate to generate energy but not the healthy cells. Therefore, the optimized conditions have been set to 5 minute incubation time under the hyperoxia microenvironment.

Example 3

Co-Culture of Healthy and Cancer Cells

Figure 2:
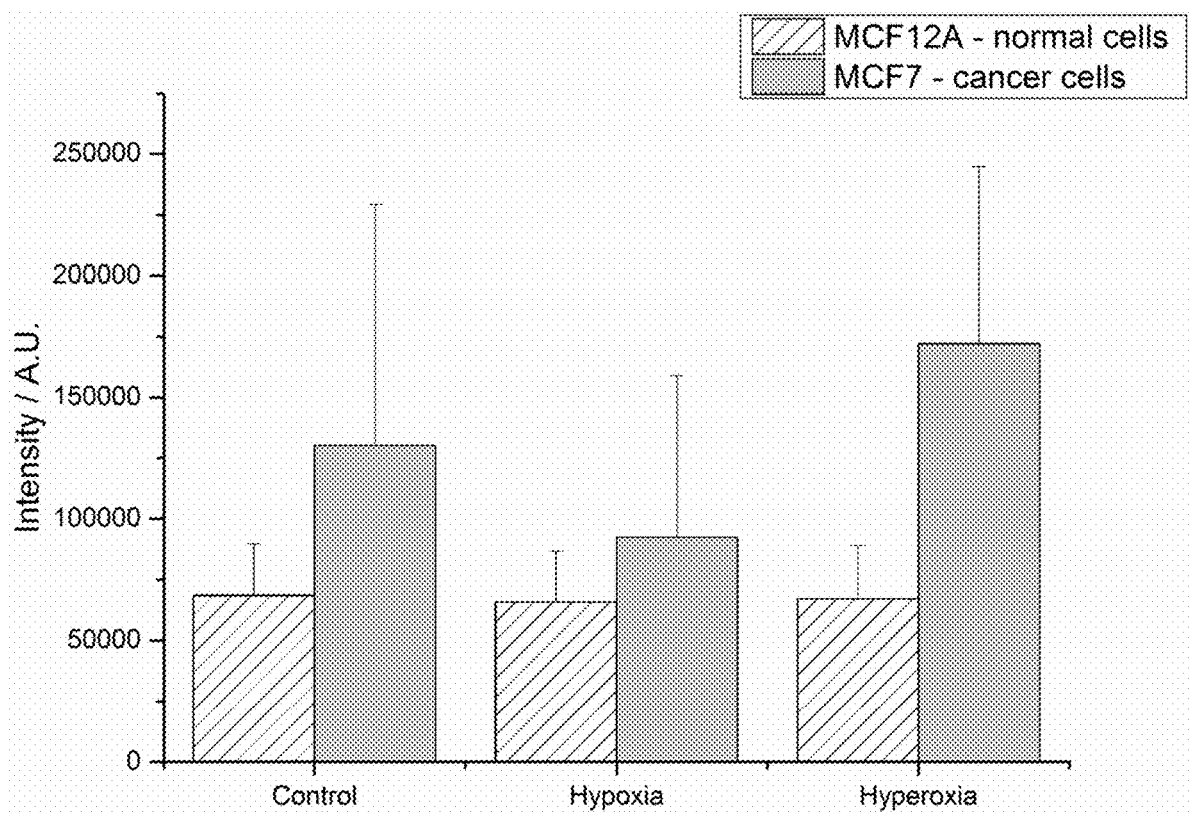
FIG. 2: Fluorescence intensities of 2-NBDG from normal and cancer cells under the standard (control) or the hypoxic or hyperoxic microenvironments. 25 cells of each cell type were counted. A.U., arbitrary units.
Figure 3:
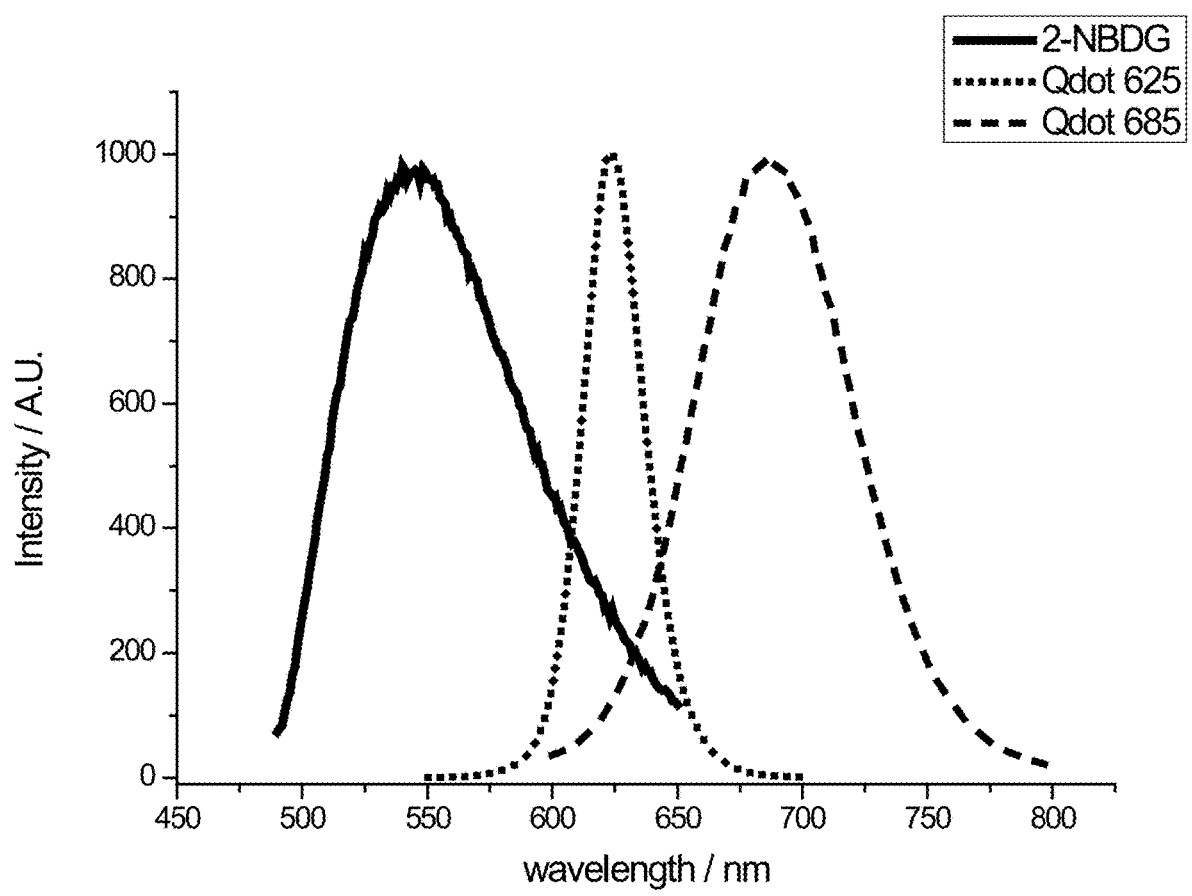
FIG. 3: Emission profiles of 2-NBDG, quantum dots (Qdot) 625 and Qdot 685, respectively. A. U., arbitrary units.
Figure 4:
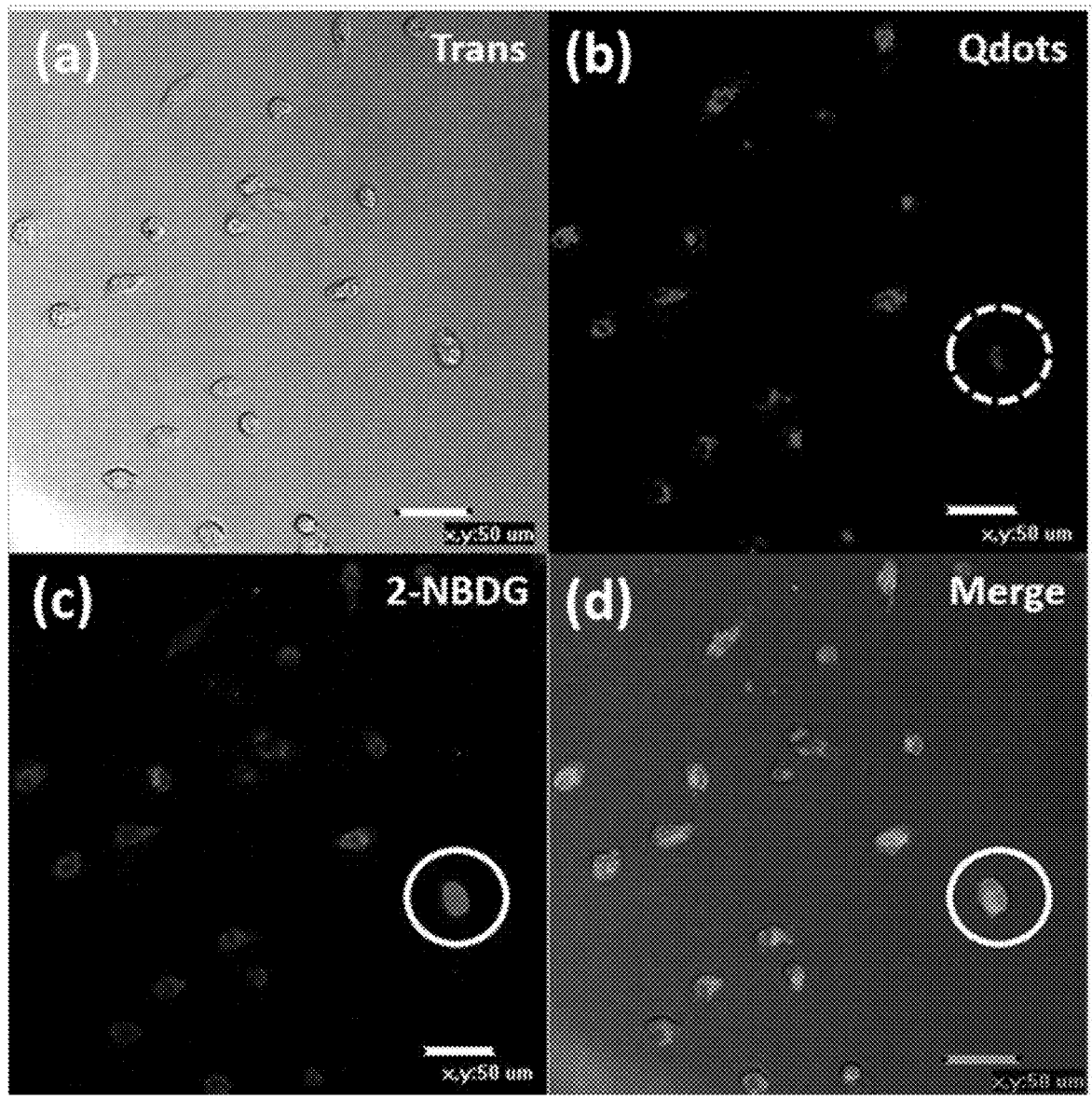
FIG. 4: a) White light image of cell mixture; (b) Fluorescence image of quantum dots using 650 nm long pass filter; the cancer cell is highlighted by dash circle; (c) Fluorescence image of 2-NBDG using the 515/30 nm filter; the one from the cancer cell is highlighted by a circle. (d) Merged image of a), b) and c); the cancer cell is highlighted by a circle.

The comparison results shown in FIG. 2 are collected from cancer and healthy breast cells separately. To further prove the proposed approach, co-cultured experiments were carried out. Healthy and cancer cells were firstly incubated with two different PEG functionalized CdSe quantum dots. (Qdot 625 for healthy and Qdot 685 for cancer cells) before being mixed. Biocompatible quantum dots were carefully chosen to avoid their emission profiles overlapping with the 2-NBDG. (FIG. 3) The cell mixture was then incubated with 300 µM of 2-NBDG at the optimized conditions for 5 minutes. FIG. 4 shows the fluorescence images of the cell mixture. In FIG. 4 (a), the white light image shows no difference between cancer and healthy cells but they can be well distinguished with the labelled quantum dots demonstrated in FIG. 4 (b). The distribution of fluorescence intensity of 2-NBDG is exhibited in FIG. 4 (c). Identified by the merged image in FIG. 4 (d), the cancer cell (highlighted by a circle) generated greater fluorescence intensity (brightness) compared to the surrounded healthy cells. This co-cultured experiment provides a solid evidence of the feasibility of the proposed strategy.

Example 4

2-NBDG Uptake Within the Microfluidic Chip

Figure 5:
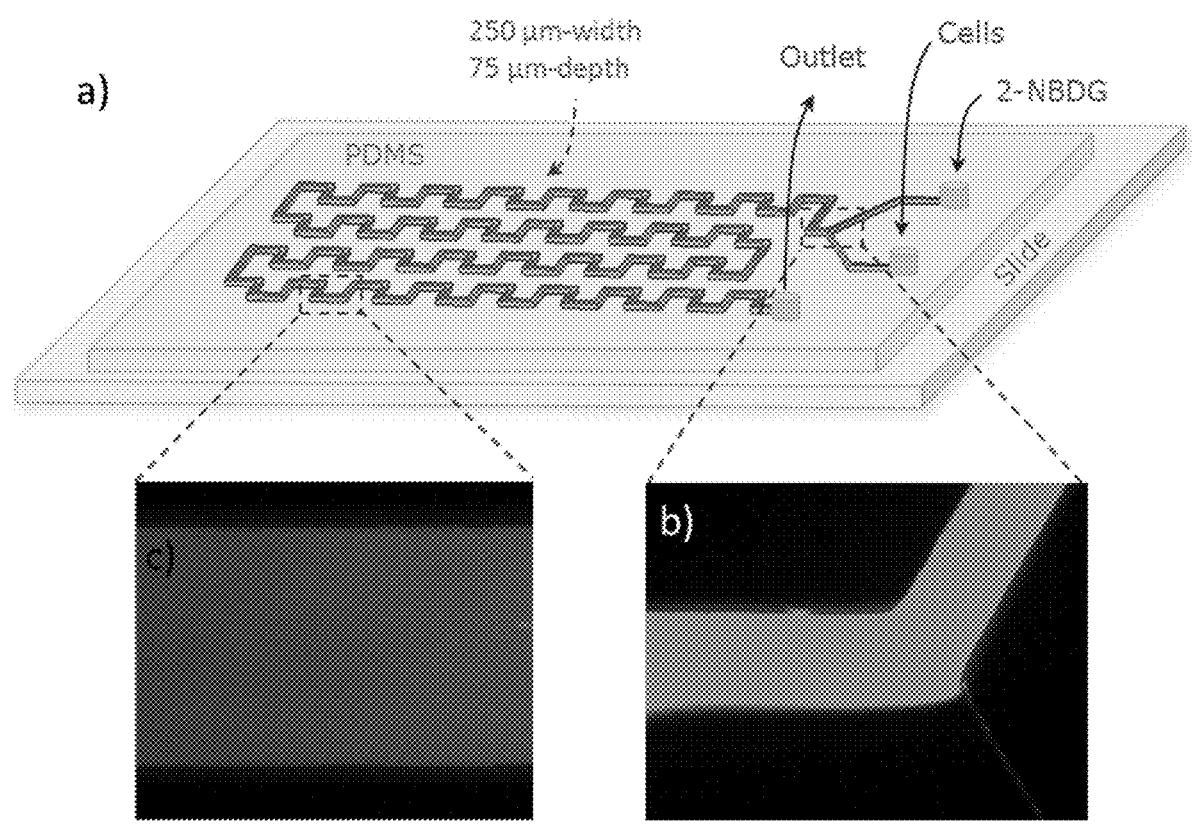
FIG. 5: a) Schematic representation of the mixing chip. b) Epi-fluorescence image from the inlet channels, where there is a clear laminar flow of cells and 2-NBDG. c) Epi-fluorescence image at the end of the central channel, where cell and 2-NBDG solutions cannot be distinguished. 2-NBDG is presented in greater brightness. PDMS, polydimethylsiloxane.

Once optimized the experimental conditions (time of exposure to 2-NBDG and hyperoxia), the whole assay was implemented in microfluidic chips to automate the procedure and make it feasible to perform in-situ measurements. To promote 2-NBDG cellular uptake, a chip consisting of a two-dimensional micromixer was employed. A flow rate of 0.05 mL/h (measured at the outlet port) was used after optimizations, which entails a total residence time of 6 min, offering thus enough time for mixing cells and 2-NBDG (as shown in FIG. 5) as well as providing the optimized incubation time of cells to ensure a maximum differentiation between the cancer and healthy cells. However, by utilizing this microfluidic chip alone, fluorescence from cells cannot be identified due to the excess amount of the fluorophore presented in the flow.

Example 5

Cell Purification Within the Microfluidic Chip

In order to minimize the interference from the excess amount of fluorophore (2-NBDG), a microfluidic chip consisting of a main channel for the concentration of cells, and ten lateral channels to remove 2-NBDG was constructed. The main microchannel had a constriction before each bifurcation microchannel to promote the preferential movement of cells along the straight central microchannel (FIG. 6b). Consequently, 2-NBDG is mainly removed from the solution through the lateral microchannels. After the purification process, cells were further diluted with 1×PBS to maintain their initial concentration and dilute the fluorophore.

The efficiency of the purification process was evaluated by comparing the fluorophore concentration of the collected cells with the one from the initial sample. 53.7±1.7% of the fluorophore was removed from the initial solution, with a minimal loss of cells (7.2±1.1%). To increase the purity of cells, the sample was recirculated into the same microsystem under the same conditions. As expected, another 54.9±1.5% of the fluorophore was eliminated. Thus, a total efficiency of ~80% was achieved through this two-step process (FIG. 6c).

Example 6

On-Line Monitoring of CTCs in the Microfluidic Chip

For the continuous on-line detection of CTCs, the design of the third microfluidic chip was based on the hydrodynamic focusing technique to allow the pass of single cells through a small width section. To this regard, three different inlet channels (one for cells and two for the buffer solution) were constructed enabling the sample being injected into the middle of the sheath flow (FIG. 8a).

To validate the hydrodynamic focusing design, stained cells were pumped into the microfluidic chip while the 2-NBDG solution acted as the sheath flow. For the formation of a two-layer stable flow, the buffer flow rate should be at least two times larger compared to the flow rate of cells. Therefore, flow rates of 0.1 and 0.2 mL/h for the central and side streams, respectively, were set to allow cells cross the section in a line. As it is shown in FIG. 8b, cells were completely focused on the center of the microchannel.

Importantly, to acquire good quality of fluorescence images of cancer and healthy cells (FIG. 8c, bottom image) in this chip for the quantification purpose, slow flow rate is desirable. To this aim, the flow rate of cells was set to 0.025 mL/h meanwhile PBS flowed at 0.075 mL/h. Images from the continuous analysis of cancer and healthy cells (done separately) were collected with an epi-fluorescence microscope (FIG. 8c). FIG. 8d shows the obtained results, where cancer cells demonstrate the higher fluorescence intensity compared to the healthy ones. These results are in concordance with the cells fixed to the substrates.

Conclusions

Liquid biopsy is playing a significant role in the cancer prognosis as well as monitor of therapy responses. The detection of circulating tumour cells (CTCs) in patient bloodstream is the core of liquid biopsy. The existing detection strategies encounter various issues such as false negatives and low specificity. Therefore, it is proposed a distinctive detection approach based on the metabolic differences between cancer and healthy cells by using the fluorophore labelled 2-D-glucose. To maximize the difference of the fluorescence intensity between cancer and healthy cells, incubation time and oxygen concentration were optimized. Importantly, under the optimized conditions, the cancer cell can be clearly identified from the surrounded healthy cells based on the greater brightness in the fluorescence image of the 2-NBDG. Implementation of the assay within the microfluidic chips (mixing, purification and detection chips) allows automating the whole procedure, being feasible for in-situ measurements, thus evolving in portable devices. The obtained results using these microsystems are in concordance with those obtained for cells fixed to the tissue culture plate, which also corroborates the robustness of the approach. The demonstrated experimental evidences provide a solid support for the approach proposed by the inventors which specifically paves the way for its application in liquid biopsy.

The invention claimed is:

1. An in vitro method for the detection of a circulating tumour cell (CTC) and/or a tumour cell (TC) in a liquid sample from a subject, and treatment of the subject, comprising the steps of:
   a) optionally, culturing the liquid sample in a cell culture medium;
   b) incubating the cells contained in the liquid sample or the cells obtained in step a) with a solution supplemented with a fluorophore-labelled metabolic indicator and saturated with oxygen, and during an appropriate time to allow the CTCs/TCs to accumulate the fluorophore-labelled metabolic indicator;
   c) removing the excess of the fluorophore-labelled metabolic indicator not accumulated in cells;
   d) measuring the fluorescence of the fluorophore-stained cells,
   wherein the detection of a fluorophore-stained cell having a fluorescence intensity superior to a control cell indicates the presence of a CTC/TC in the liquid sample, and
   e) treating the subject from whom the CTC/TC has been detected in the liquid sample, with a treatment comprising at least one selected from the group consisting of chemotherapy, immunotherapy, hormonal therapy, radiation therapy, and surgery.

2. The method according to claim 1, wherein the fluorophore-labelled metabolic indicator is 2-(N-(7-nitrobenz-2-oxa-1,3-diazol-4-yl)amino)-2-deoxyglucose (2-NBDG).

3. An in vitro method for diagnosing a tumour and/or metastasis in a subject comprising detecting the presence of a CTC/TC in a biofluid sample of said subject by a method according to claim 1 wherein if the presence of a CTC/TC in a biofluid sample of said subject is detected, then the subject suffers from a tumour and/or metastasis.

4. An in vitro method for determining the prognosis or for monitoring the progression of a cancer and/or metastasis in a subject, comprising detecting and quantifying the presence of a CTC/TC in a biofluid sample of said subject by a method according to claim 1 and comparing the number of CTCs/TCs in the biofluid sample of said subject with the number of CTCs/TCs in a reference sample obtained from the same subject at an earlier time of point of the disease
   wherein a decrease in the number of CTCs/TCs with respect to the same number in the reference sample is indicative that the subject has a good prognosis, or
   wherein an increase in the number of CTCs/TCs with respect to the same number in the reference sample is indicative that the subject has a poor prognosis.

* * * * *

UNITED STATES PATENT AND TRADEMARK OFFICE
CERTIFICATE OF CORRECTION

Page 1 of 1

PATENT NO. : 10,987,669 B2
APPLICATION NO. : 16/081720
DATED : April 27, 2021
INVENTOR(S) : Hainan Xie et al.

It is certified that error appears in the above-identified patent and that said Letters Patent is hereby corrected as shown below:

On the Title Page

Page 2, Item (56) References Cited, OTHER PUBLICATIONS, in the listing of the third to last reference, "Zheng, D., et al." should be -- Zhang, D., et al. --.

In the Specification

Column 23, Line 14, "(2-N BDG)" should be -- (2-NBDG) --.

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*